United States Patent
Tanzer et al.

[11] Patent Number: 5,853,403
[45] Date of Patent: Dec. 29, 1998

[54] ABSORBENT ARTICLE WITH BODY CONTACTING LIQUID CONTROL MEMBER

[75] Inventors: Richard Warren Tanzer; Barbara Ann Gossen, both of Neenah; Dan Darold Endres, Appleton; Cynthia Helen Nordness, Oshkosh; Paula Mary Sosalla, Appleton, all of Wis.

[73] Assignee: Kimberly-Clark Worldwide, Inc., Neenah, Wis.

[21] Appl. No.: 635,816

[22] Filed: Apr. 19, 1996

Related U.S. Application Data

[63] Continuation-in-part of Ser. No. 328,987, Oct. 25, 1994, abandoned.
[51] Int. Cl.[6] ................................................ N61F 13/15
[52] U.S. Cl. .................. 604/385.1; 604/378; 604/385.2
[58] Field of Search ..................................... 604/358, 378, 604/385.1–387, 383, 393, 394, 389–391

[56] References Cited

U.S. PATENT DOCUMENTS

| | | | |
|---|---|---|---|
| Re. 31,922 | 6/1985 | Mesek et al. | 604/385.2 |
| D. 342,997 | 1/1994 | Buck et al. | D24/126 |
| 2,277,043 | 3/1942 | Cohn . | |
| 3,828,785 | 8/1974 | Gamm et al. . | |
| 3,901,238 | 8/1975 | Gellert | 604/366 |
| 3,902,236 | 9/1975 | Deem . | |
| 4,076,663 | 2/1978 | Masuda et al. . | |
| 4,286,082 | 8/1981 | Tsubakimoto et al. . | |
| 4,496,360 | 1/1985 | Joffe et al. | 604/397 |
| 4,578,079 | 3/1986 | Buell | 604/379 |
| 4,578,073 | 3/1986 | Dysart et al. | 604/397 |
| 4,579,556 | 4/1986 | McFarland | 604/385.2 |
| 4,597,760 | 7/1986 | Buell | 604/397 |
| 4,597,761 | 7/1986 | Buell | 604/397 |
| 4,598,528 | 7/1986 | McFarland et al. . | |
| 4,643,726 | 2/1987 | Gegelys | 604/368 |
| 4,650,438 | 3/1987 | Joffe | 604/390 |
| 4,662,877 | 5/1987 | Williams | 604/385.2 |
| 4,668,230 | 5/1987 | Damico et al. | 604/385.2 |
| 4,671,793 | 6/1987 | Hults et al. | 604/385 |
| 4,699,823 | 10/1987 | Kellenberger et al. . | |
| 4,704,116 | 11/1987 | Enloe | 604/385.2 |
| 4,710,187 | 12/1987 | Boland et al. | 604/385.2 |

(List continued on next page.)

FOREIGN PATENT DOCUMENTS

| | | |
|---|---|---|
| 0 098 512 A2 | 1/1984 | European Pat. Off. . |
| 0 321 985 A3 | 6/1989 | European Pat. Off. . |
| 0339461 | 11/1989 | European Pat. Off. . |
| 0 359 410 | 3/1990 | European Pat. Off. ........ A61F 13/15 |
| 0386816 | 9/1990 | European Pat. Off. . |
| 0 567 792 | 11/1993 | European Pat. Off. ........ A61F 13/15 |
| 0382022 | 1/1994 | European Pat. Off. . |
| 0601610 | 6/1994 | European Pat. Off. . |
| 0615737 | 9/1994 | European Pat. Off. . |
| 0619953 | 10/1994 | European Pat. Off. . |
| 0627177 | 12/1994 | European Pat. Off. . |
| 0627178 | 12/1994 | European Pat. Off. . |
| 0661031 | 7/1995 | European Pat. Off. . |
| 0679754 | 9/1952 | United Kingdom . |
| 0774712 | 5/1957 | United Kingdom . |
| 0779461 | 7/1957 | United Kingdom . |
| 0849573 | 9/1960 | United Kingdom . |
| 2256803 | 12/1992 | United Kingdom . |
| 2268073 | 1/1994 | United Kingdom . |
| 2275611 | 9/1994 | United Kingdom . |
| 2 284 741 A | 6/1995 | United Kingdom . |
| 2284550 | 6/1995 | United Kingdom . |
| 2 294 398 A | 5/1996 | United Kingdom . |
| 90/08524 | 8/1990 | WIPO . |
| 93/25170 | 12/1993 | WIPO . |
| 94/14394 | 7/1994 | WIPO . |
| 95 16421 | 6/1995 | WIPO ........................... A61F 13/15 |
| 95/16418 | 6/1995 | WIPO . |
| 95/16419 | 6/1995 | WIPO . |

*Primary Examiner*—Mark O. Polutta
*Attorney, Agent, or Firm*—Thomas M. Gage

[57] ABSTRACT

An absorbent article, such as a diaper, includes a liquid control member formed of a liquid permeable material adapted to remain in contact with the urethral region of the wearer regardless of the position or movements of the wearer.

11 Claims, 9 Drawing Sheets

U.S. PATENT DOCUMENTS

| | | | |
|---|---|---|---|
| 4,753,649 | 6/1988 | Pazdernik | 604/389 |
| 4,770,298 | 9/1988 | McFarland et al. | 206/390 |
| 4,772,282 | 9/1988 | Oakley | 604/385.1 |
| 4,773,906 | 9/1988 | Krushel | 604/391 |
| 4,808,176 | 2/1989 | Kielpikowski | 604/385.2 |
| 4,834,737 | 5/1989 | Khan | 604/385.2 |
| 4,892,536 | 1/1990 | DesMarais et al. | 604/385.2 |
| 4,892,598 | 1/1990 | Stevens et al. | |
| 4,938,756 | 7/1990 | Salek | 604/368 |
| 4,955,880 | 9/1990 | Rodriguez | 604/393 |
| 4,961,736 | 10/1990 | McCloud | 604/385.1 |
| 4,964,857 | 10/1990 | Osborn | 604/395 |
| 4,968,312 | 11/1990 | Khan | 604/385.1 |
| 5,074,854 | 12/1991 | Davis | 604/385.1 |
| 5,108,385 | 4/1992 | Snyder | 604/397 |
| 5,147,343 | 9/1992 | Kellenberger | 604/368 |
| 5,167,654 | 12/1992 | Yang | 604/385.2 |
| 5,171,236 | 12/1992 | Drei er et al. | 604/369 |
| 5,185,011 | 2/1993 | Strasser | 604/385.1 |
| 5,207,662 | 5/1993 | James | 604/385.2 |
| 5,217,447 | 6/1993 | Gagnon | 604/397 |
| 5,221,277 | 6/1993 | Beplate | 604/394 |
| 5,236,428 | 8/1993 | Zajaczkowski | 604/385.2 |
| 5,261,901 | 11/1993 | Guay | 604/391 |
| 5,269,775 | 12/1993 | Freeland et al. | 604/385.2 |
| 5,342,340 | 8/1994 | Kichefski et al. | 604/385.1 |
| 5,360,422 | 11/1994 | Brownlee et al. | 604/385.2 |
| 5,389,095 | 2/1995 | Suzuki et al. | 604/385.2 |
| 5,405,342 | 4/1995 | Roessler et al. | 604/364 |
| 5,409,476 | 4/1995 | Coates | 604/391 |
| 5,417,680 | 5/1995 | Kimura et al. | 604/385.2 |
| 5,486,166 | 1/1996 | Bishop et al. | 604/366 |
| 5,490,846 | 2/1996 | Ellis et al. | 604/366 |

ABSORBENT ARTICLE WITH BODY CONTACTING LIQUID CONTROL MEMBER

This application is a continuation-in-part of U.S. patent application Ser. No. 08/328,987 filed Oct. 25, 1994, abandoned.

BACKGROUND OF THE INVENTION

The present invention relates to articles for absorbing body fluids. More particularly, the invention pertains to an absorbent article having a liquid control member that resides against the body of the wearer while the article is worn. The invention also pertains to methods of making such absorbent articles.

Conventional disposable absorbent articles have typically included a liquid previous bodyside liner, a liquid impervious backing sheet, and an absorbent material disposed between the bodyside liner and the backing sheet. An attachment system is also included to secure the product about the body of the wearer.

To improve the fit of the absorbent article about the wearer, elastic materials have also been incorporated in conventional absorbent articles. Most commonly, such elastic materials have included threads, strands, or ribbons of elastic bonded to the backing sheet, either along the longitudinal sides or the longitudinal ends of the product.

In disposable absorbent articles of the foregoing type, even those incorporating elastic materials, the product is not held against the urethral area of the wearer. Consequently, expelled liquid may not be controlled and can run along the wearer's legs or splash away from the surface of the product. Product performance therefore can be dependent on the elastic seals formed against the body.

Therefore, what is lacking and needed in the art is an absorbent article that controls liquid voids from the point at which they are expelled, so that liquid is not permitted to run uncontrolled over the surface of the article.

SUMMARY OF THE INVENTION

In response to the discussed deficiencies in the prior art, a new absorbent article has been developed. The absorbent article provides for the control of liquid from the point of urination, regardless of whether the wearer is standing, sitting or lying down.

In one aspect, the invention pertains to an absorbent article having a longitudinal axis, an elongate length, a first waistband region, a second waistband region, and an intermediate region interconnecting the first and second waistband regions. The absorbent article includes a garment shell comprising a backsheet layer, an absorbent assembly disposed on the backsheet layer, and a bodyside layer bonded to the backsheet layer and sandwiching the absorbent assembly therebetween. The absorbent article also includes a liquid control member having a first stationary zone bonded to the bodyside layer in the first waistband region, an opposite second stationary zone bonded to the bodyside layer in the second waistband region, and an elasticized zone between the first and second stationary zones. The elasticized zone of the liquid control member is adapted to contract at least about 10 percent of the elongate length. The liquid control member includes a liquid permeable liquid handling layer in substantially direct liquid contact with the absorbent assembly. The liquid control member is adapted to permit liquid to drain through the liquid handling layer into the absorbent assembly. At least one elastic member is disposed between the liquid handling layer and the bodyside layer.

The liquid control member is adapted to remain in contact with the urethral region of the wearer regardless of the position or movements of the wearer. Expelled liquid immediately contacts the liquid control member and is therefore not allowed to run freely throughout the diaper. The liquid can be channeled and/or directed to the absorbent assembly of the garment shell. Beneficially, the absorbent article need not rely primarily on elasticized leg and waistbands or containment flaps for urine containment.

In another aspect, the invention concerns an absorbent article including a backsheet layer, an absorbent assembly disposed on the backsheet layer, and a liquid control assembly superposed on the backsheet layer with the absorbent assembly disposed between the backsheet layer and the liquid control assembly. The liquid control assembly includes a liner assembly having a pair of lateral panels and a liquid permeable center panel disposed between the lateral panels. The lateral panels are bonded to the backsheet layer and the center panel is adapted to move relative to the absorbent assembly. A liquid handling layer, which is adapted to rapidly take in liquid and to then more slowly discharge the liquid into the underlying absorbent assembly, is bonded to the center panel. A pair of liner elastic members are operatively joined to the center panel with the liquid handling layer disposed between the liner elastic members. The liner elastic members are adapted to contract the center panel and space the center panel away from the absorbent assembly when in a relaxed condition.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
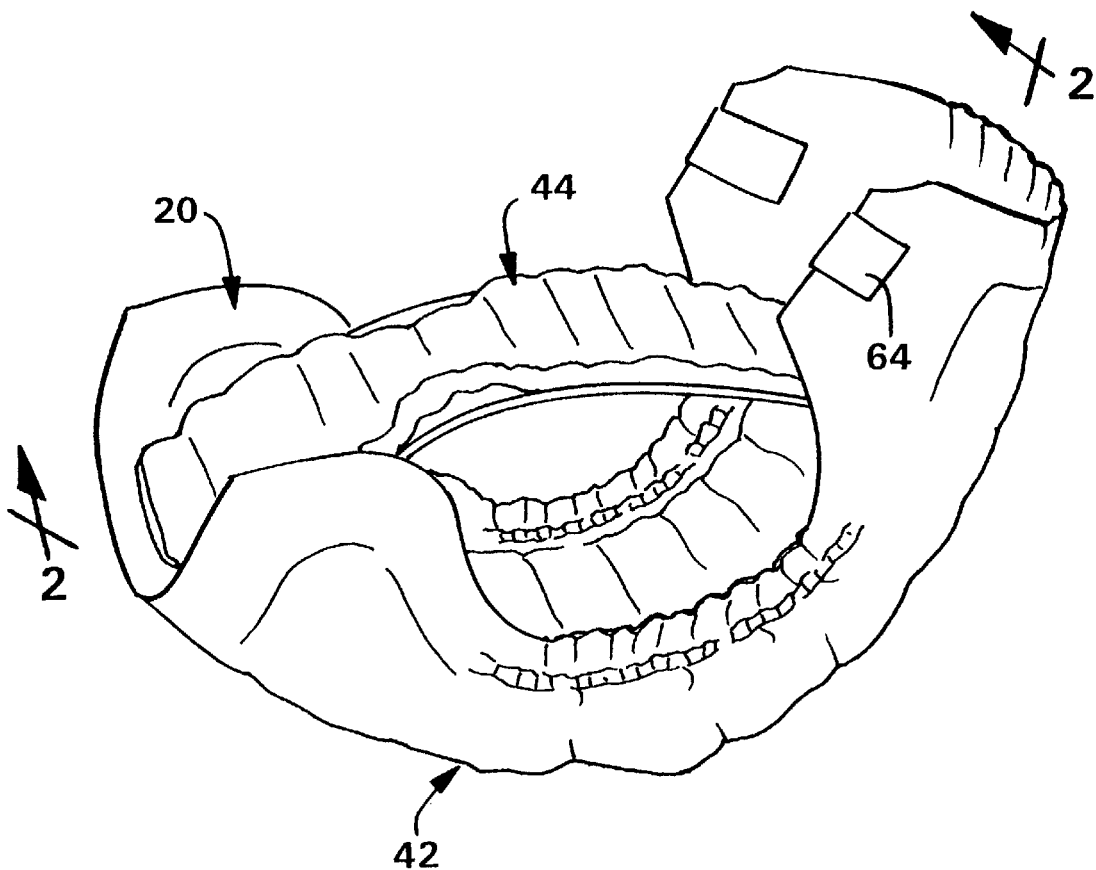
FIG. 1 representatively shows a perspective view of a disposable absorbent article according to the present invention.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposed," "disposed on," "disposed with," "disposed at," "disposed near" and variations thereof are intended to mean that one element can be integral with another element, or that one element can be a separate structure bonded to or placed with or placed near another element.

(c) "elastic," "elasticized" and "elasticity" mean that property of a material by virtue of which it tends to recover its original size and shape after removal of a force causing a deformation.

(d) "elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

(e) "extension," "extend" and "extended" mean the change in length of a material due to stretching, expressed in units of length.

(f) "elongation" means the ratio of the extension of a material to the length of a material prior to stretching, expressed in percent.

(g) "fabrics" is used to refer to all of the woven, knitted and nonwoven fibrous webs.

(h) "flexible" refers to materials which are compliant and which will readily conform to the general shape and contours of the wearer's body.

(i) "force" includes a physical influence exerted by one body on another which produces acceleration of bodies that are free to move and deformation of bodies that are not free to move. Force is expressed in grams force (1 gram force is equal to 0.000102 Newtons).

(j) "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(k) "inward" and "outward" refer to positions relative to the center of an absorbent garment, and particularly transversely and/or longitudinally closer to or away from the longitudinal and transverse center of the absorbent garment.

(l) "layer" when used in the singular can have the dual meaning of a single element or a plurality of elements.

(m) "liquid communication" means that liquid such as urine is able to travel from one layer to another.

(n) "liquid impermeable" when used to describe a layer or laminate means that liquid such as urine will not pass through the layer or laminate under ordinary use conditions in a direction generally perpendicular to the plane of the layer or laminate at the point of liquid contact.

(o) "member" when used in the singular can have the dual meaning of a single element or a plurality of elements.

(p) "nonwoven web" means a web of material which is formed without the aid of a textile weaving or knitting process.

(q) "operatively joined" and "operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(r) "rupture" means the breaking or tearing apart of a material; in tensile testing, the term refers to the total separation of a material into two parts either all at once or in stages, or the development of a hole in some materials.

(s) "stretch bonded" refers to an elastic member being bonded to the another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

(t) "stretch bonded laminate" refers to composite material having at least two layers in which one layer is a gatherable layer and the other layer is an elastic layer. The layers are joined together when the elastic layer is in an extended condition so that upon relaxing the layers, the gatherable layer is gathered.

(u) "unadhered" refers to an absence of bonds of sufficient strength to withstand the forces typically encountered during ordinary wearing of the diaper.

These terms may be defined with additional language in the remaining portion of the specification.

DETAILED DESCRIPTION OF THE PREFERRED EMBODIMENTS

Figure 2:
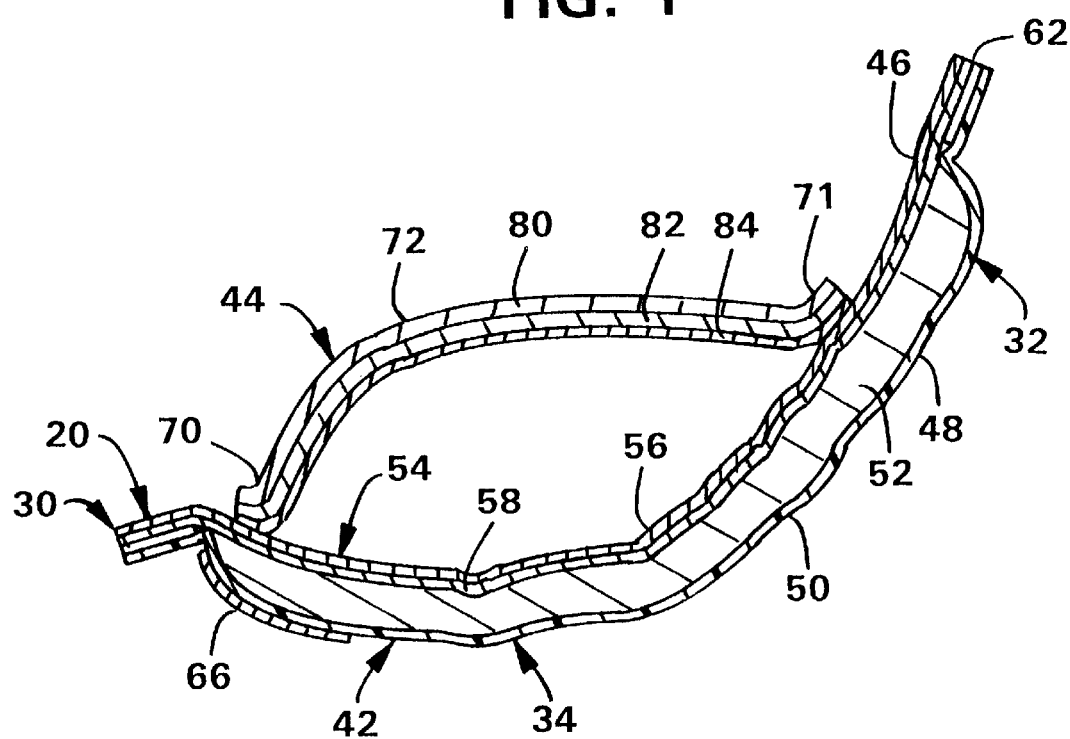
FIG. 2 representatively shows a longitudinal section view taken generally from the plane of the line 2—2 in FIG. 1, illustrating the relationship of a liquid control member and a garment shell of the absorbent article.
Figure 3:
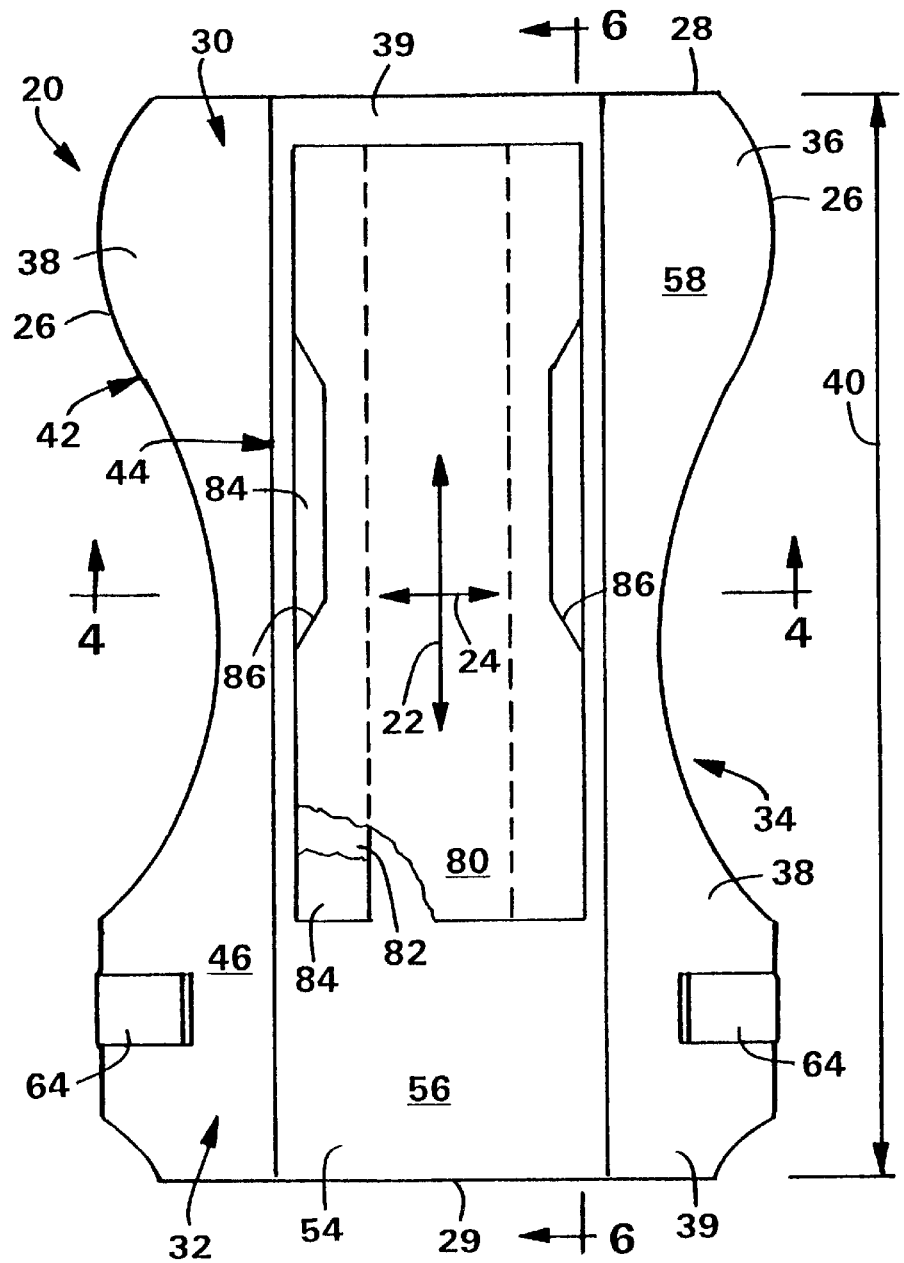
FIG. 3 representatively shows a top plan view of the absorbent article of FIG. 1 but in a stretched flat condition and with the liquid control member partially cut-away for purposes of illustration.

With reference to FIGS. 1–3, an absorbent article formed according to the present invention is shown for purposes of illustration as a disposable diaper 20. The invention may also be embodied in other types of absorbent articles such as adult incontinence garments, feminine napkins, children's training pants, or the like.

The illustrated diaper 20 defines a longitudinal axis, represented by arrow 22 in FIG. 3, and a transverse axis, represented by arrow 24 in FIG. 3. The diaper 20 has opposite longitudinal side edges 26, a first or front end edge 28, and a second or back end edge 29. The front and back end edges 28 and 29 extend between the opposite side edges 26. The diaper 20 includes a first or front waistband region 30, a second or back waistband region 32, and an intermediate, crotch region 34 positioned between and interconnecting the front and back waistband regions. The outer edges of the diaper 20 define a periphery 36 in which the longitudinally extending side margins are designated 38 and the laterally extending end margins are designated 39. The side edges 26 define leg openings for the diaper 20, and optionally, are curvilinear and contoured. The end edges 28 and 29 are shown as generally straight, but optionally, may be curvilinear.

The diaper 20 has a length dimension measured between the front and back end edges 28 and 29 along the longitudinal axis 22. The length dimension of the diaper 20 is determined with any elastic components of the diaper in a stretched state and is thus hereinafter referred to as the elongate length of the diaper. The elongate length is representatively illustrated by arrow 40 in FIG. 3.

One suitable method for determining the elongate length 40 is to hang the diaper 20 vertically adjacent a flat, vertical surface. The diaper 20 is hung with the back waistband region 32 above the front waistband region 30 and with the surface intended to face the wearer during use positioned toward the flat, vertical surface. The top end margin 39 of the diaper 20 is held horizontal with two or more clamps. The clamps are positioned to avoid if possible any absorbent batt of the diaper, and so that any leg elastics of the diaper are centered between the outermost clamps. Any waist elastic present in the diaper is fully stretched prior to securing the clamps. The diaper is straightened and extended by gently running your fingers down the side margins 38, and particularly along any leg elastics. Weights are attached to the lower end margin 39 and gently lowered to hang freely. The weights should be sufficient to completely stretch the longitudinally oriented elastic components of the garment shell of the diaper, provided however that no components of the diaper begin to rupture. For a medium size diaper, an evenly distributed load of 1000 grams is appropriate. Verify that the diaper is extended by again gently running your fingers down the side margins 38. The elongate length 40 is then determined by measuring the distance between the front and back end edges 28 and 29 along the longitudinal axis 22.

The front waistband region 30 is contiguous with the front end edge 28 and extends longitudinally inward therefrom toward the transverse center line of the diaper 20 along a distance of from about 2 to about 20 percent of the elongate length. The back waistband region 32 is contiguous with the back end edge 29 and extends longitudinally inward therefrom toward the transverse center line along a distance of from about 2 to about 35 percent of the elongate length. The waistband regions 30 and 32 comprise those upper portions of diaper 20 which, when worn, wholly or partially cover or encircle the waist or mid-lower torso of the wearer. The intermediate, crotch region 34 comprises that portion of diaper 20 which, when worn, is positioned between the legs of the wearer and covers the lower torso of the wearer. Thus, the crotch region 34 is the area where liquid insults typically occur in the diaper or other disposable absorbent article.

In one aspect of the invention, the diaper 20 includes a garment shell 42 and a liquid control member 44. The liquid control member 44 is adapted to remain in contact with the urethral region of the baby when the diaper 20 is worn. The garment shell 42 has an inner surface 46 to which the liquid control member 44 is operatively connected, and an opposite outer surface 48.

In the illustrated embodiment, the garment shell 42 includes a substantially liquid impermeable backsheet layer 50, an absorbent assembly 52 disposed on the backsheet layer, and a substantially liquid permeable bodyside layer 54 bonded to the backsheet layer to sandwich the absorbent assembly therebetween. The bodyside layer 54 as illustrated includes a surge management portion 56 and a full-width liner 58. The backsheet layer 50 and bodyside layer 54 are desirably longer and wider than the absorbent assembly 52 so that the peripheries of the backsheet layer and bodyside layer may be bonded together using ultrasonic bonds, thermal bonds, adhesives, or other suitable means, and form the side and end margins 38 and 39. The absorbent assembly 52 may also be bonded directly to the backsheet layer 50 and/or the bodyside layer 54 using ultrasonic bonds, thermal bonds, adhesives, or other suitable means.

Figure 5:
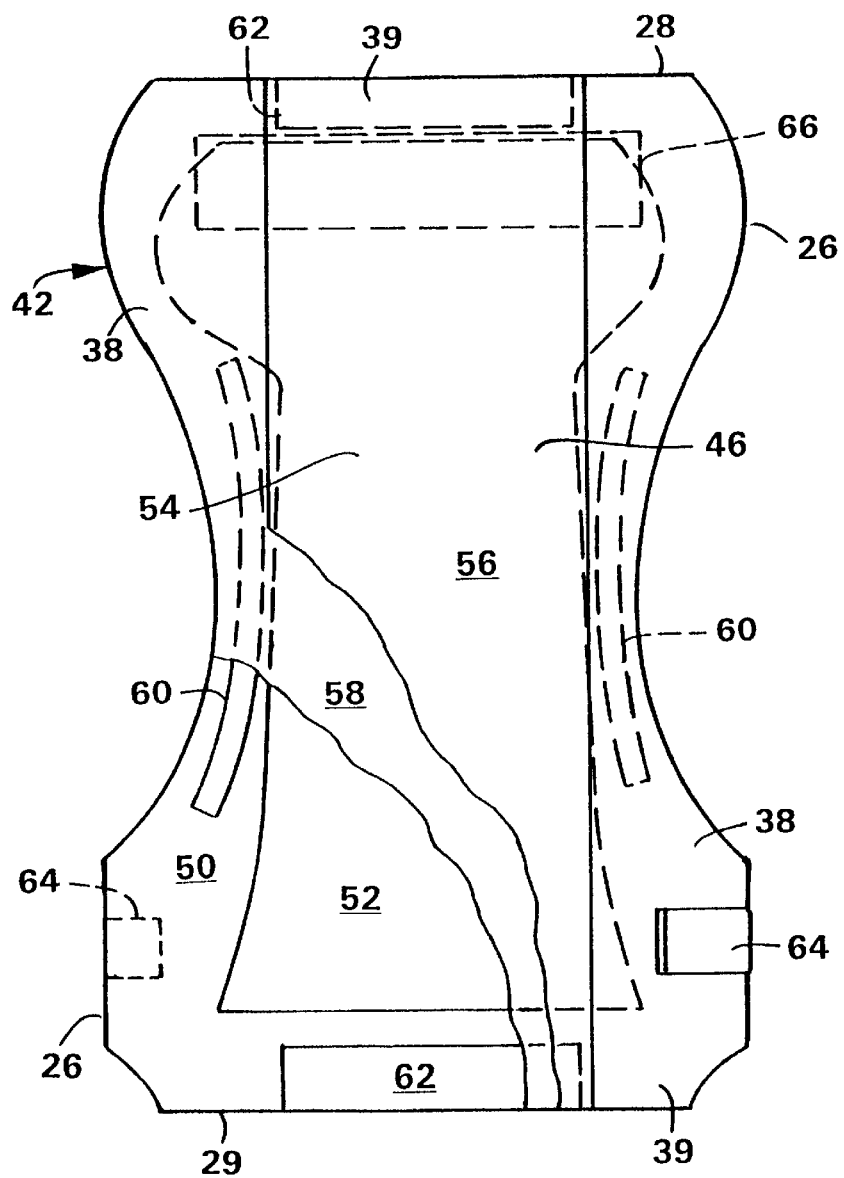
FIG. 5 representatively shows a partially cut-away, top plan view of the garment shell of the absorbent article shown in FIGS. 1–4.

The garment shell 42 of the diaper 20 is illustrated in a stretched condition and by itself, that is without the liquid control member 44, in FIG. 5. As illustrated, the garment shell 42 has an hourglass or I shape. Of course, the garment shell 42 may optionally be T-shaped, rectangular, or irregularly-shaped. The general shape of the absorbent assembly 52 may correspond to the shape of the garment shell 42 or assume a different shape. Desirably, the garment shell 42 also includes elastic members in several locations to maintain the periphery 36 of the diaper 20 against the wearer and minimize the potential for leakage. Elongated leg elastic members 60 are longitudinally orientated in each side margin 38, extending toward the front and back end edges 28 and 29. The leg elastic members 60 are positioned between the backsheet layer 50 and the liner 58. Using ultrasonic bonds, adhesives, thermal bonds, or other suitable means, the leg elastic members 60 are attached in a stretched condition to the backsheet layer 50, the liner 58, or both, in either a straight or a curved shape. The leg elastic members 60 can be arranged to draw and hold the side margins 38 of the diaper 20 against the legs of the wearer and form a seal therewith.

The garment shell 42 may also include waist elastic members 62 (FIG. 5) in the end margins 39. The waist elastic members 62 are longitudinally oriented parallel to the transverse axis 24 of the diaper 20 to provide elasticized waistbands. Desirably, the waist elastic members 62 are positioned between the backsheet layer 50 and the liner 58 and secured in an extended condition to both the backsheet layer and the liner, using ultrasonic bonds, adhesives, thermal bonds or other suitable means.

Refastenable tape members 64 (FIGS. 1, 3 and 5) are operably connected to the side margins 38 in the back waistband region 32 of the diaper 20. Each tape member 64 includes a fastening strip that may be releasably attached to an optional tape landing pad 66 (FIGS. 2 and 5) located in the front waistband region 30. The landing pad 66 is fixed by adhesive or other suitable means to the surface of the backsheet layer 50 that is remote from the absorbent assembly 52. The tape members 64 and the landing pad 66 are positioned so that the fastening strips may be attached to the landing pad when the diaper 20 is secured on a baby.

The tape members 64 and the landing pad 66 may be formed of a polypropylene film and may be constructed in a manner as disclosed in U.S. Pat. No. 4,753,649 issued Jun. 28, 1988, to Pazdernik, which is incorporated herein by reference to the extent it is consistent herewith. Other suitable fastening devices, such as hooks, snaps, cohesive strips and the like, could be used in place of the tape members 64 and the landing pad 66.

In general, the backsheet layer 50, absorbent assembly 52, bodyside layer 54, elastic members 60 and 62, and fastening system components 64 and 66 of the garment shell 42 may be assembled in a variety of well-known diaper configurations. Further, the garment shell 42 may include other components in addition to those specifically illustrated in diaper 20. In particular, alternative diaper configurations which include additional features are disclosed in U.S. patent application Ser. No. 08/168,615 by T. Roessler et al., filed Dec. 16, 1993, and titled "Dynamic Fitting Diaper" (Attorney Docket No. 10,961); and U.S. patent application Ser. No. 08/168,615 by E. D. Johnson et al., filed Aug. 12, 1994, and titled "Diaper With Improved Lateral Elongation Characteristics" (Attorney Docket No. 11,629).

The liquid control member 44 is designed to stay in contact with the urethral region of the wearer regardless of the position or movements of the wearer. In current products not held against the urethral area of the wearer, liquid may run toward the ends or sides of the product before contacting the product. For example, liquid may run along the skin of the wearer. Under such circumstances, performance of the product is highly dependent on the seals formed against the body by peripheral components such as waist and leg elastics. When a waist or leg seal fails, leakage can occur despite the absorbent structure of the product not having reached its potential capacity. In the present invention, the liquid control member 44 is adapted to maintain contact with the urethral region of the wearer and control the input of liquid to the absorbent assembly 52. These aspects of the present invention will now be described in greater detail.

The liquid control member 44 includes a first stationary zone 70, an opposite second stationary zone 71, and an elasticized zone 72 positioned between and interconnecting the first and second stationary zones. With particular reference to FIG. 2, the first stationary zone 70 is bonded to the inner surface 46 of the garment shell 42 in the front waistband region 30. The second stationary zone 71 is bonded to the inner surface 46 in the back waistband region 32. The elasticized zone 72, however, is unadhered to the inner surface 46. The liquid control member 44 may be bonded to the garment shell 42 using ultrasonic bonds, adhesives, thermal bonds, or other suitable means.

Figure 6:
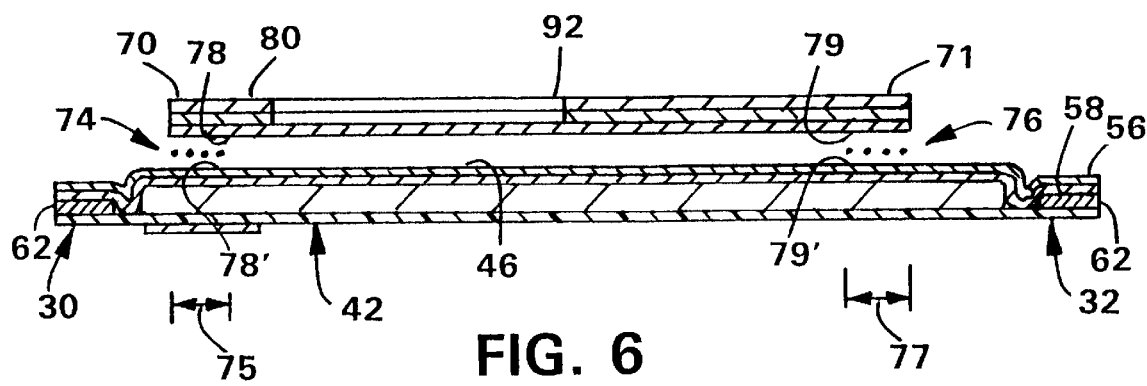
FIG. 6 representatively shows a longitudinal section view of the components of the absorbent article shown in FIG. 1, taken generally from the plane of the line 6—6 in FIG. 3, but at an intermediate stage of assembly.

The diaper 20 is illustrated in FIG. 6 at an intermediate stage of assembly, and in particular where the garment shell 42 and liquid control member 44 have been separately assembled but not yet connected. The liquid control member 44 is shown arranged in a stretched condition for attachment. As illustrated, a pattern of adhesive 74 is used to bond the first stationary zone 70 to the front waistband region 30. The adhesive 74 defines a first bond region representatively shown by arrow 75 over which the first stationary zone 70 is bonded to the inner surface 46. Similarly, a pattern of adhesive 76 is employed to bond the second stationary zone 71 to the back waist waistband region 32. The location of the adhesive 76 defines a second bond region representatively shown by arrow 77.

The boundaries between the various zones 70, 71, and 72 of the liquid control member 44 are determined by the locations at which the liquid control member is bonded to the inner surface 46. With continuing reference to FIG. 6, the first stationary zone 70 is generally that portion of the liquid control member 44 that is bonded to the inner surface 46 in the front waistband region 30. In particular, the portion of the first bond region 75 that is longitudinally closest to the transverse axis 24 of the garment 20 is designated inward bond point 78. The first stationary zone 70 comprises all portions of the liquid control member 44 corresponding to and longitudinally outward from the inward bond point 78.

Likewise, the portion of the second bond region 77 that is longitudinally closest to the transverse axis 24 is designated inward bond point 79. The second stationary zone 71 corresponds to that portion of the liquid control member 44 that is bonded to the inner surface 46 in the back waistband region 32, and in particular all portions of the liquid control member corresponding to and located longitudinally outward from the inward bond point 79. Inward bond points 78 and 79 are illustrated in FIG. 6 on a surface of the liquid control member 44. When the liquid control member 44 is brought in contact with the inner surface 46, however, it can be appreciated that inward bond points 78' and 79' on the inner surface 46 correspond to the inward bond points 78 and 79, respectively, on the liquid control member 44.

The elasticized zone 72 corresponds to the portion of the liquid control member 44 that is between the inward bond points 78 and 79. The elasticized zone 72 of the liquid control member 44 is not directly bonded to the garment shell 42 and is thus capable of moving relative to the inner surface 46. In fact, the liquid control member 44 is desirably stretch bonded to the garment shell 42 so that the elasticized zone 72 is free to contract and expand longitudinally as necessary to stay in contact with the urethral region of the wearer when the diaper 20 is worn. Desirably, the elasticized zone 72 is adapted to contract the diaper 20 at least about 10 percent of the elongate length 40, particularly at least about 25 percent of the elongate length, and more particularly at least about 40 percent of the elongate length for improved performance.

The elasticized zone 72 is adapted to expand and contract as necessary to remain in contact with the urethral region of the wearer. A diaper 20 is typically positioned on a baby so that the front end edge 28 is adjacent the belly button and the back end edge 29 is adjacent the small of the baby's back. The diaper 20 thus covers a portion of the baby having a distance measured along the baby's skin which will be referred to as the belly button to back distance. To allow for sufficient urine and fecal capacity, such as about 400 cc, the diapers are not "skin tight" and the elongate length 40 of a diaper is typically longer than the belly button to back distance. Further, the belly button to back distance changes depending upon the position of the wearer. This is illustrated in Table 1 below, which reports the measurements of four babies.

TABLE 1

Infant Measurements

| Subject | Position | Belly Button To End of Penis | Belly Button To Back | Waist Circumference |
|---|---|---|---|---|
| Male 1 | Standing | 3.5 in (9 cm) | 14 in (35.9 cm) | 18 in (46.2 cm) |
|  | Sitting | 1.5 in (3.8 cm) | 11.75 in (30.1 cm) | 21 in (53.8 cm) |
|  | Lying Down | 3.5 in (9 cm) | 14 in (35.9 cm) | 18.5 in (47.4 cm) |
| Male 2 | Standing | 3.5 in (9 cm) | 12 in (30.8 cm) | 17 in (43.6 cm) |
|  | Sitting | 2.5 in (6.4 cm) | 10.5 in (26.9 cm) | 18.25 in (46.8 cm) |
|  | Lying Down | 3.5 in (9 cm) | 12 in (30.8 cm) | 17.5 in (44.9 cm) |

| Subject | Position | Belly Button To Vaginal Opening | Belly Button To Back | Waist Circumference |
|---|---|---|---|---|
| Female 1 | Standing | 4.5 in (11.5 cm) | 11.25 in (28.8 cm) | 15.5 in (39.7 cm) |
|  | Sitting | 2.25 in (5.8 cm) | 9.0 in (23.1 cm) | 16.5 in (42.3 cm) |
|  | Lying Down | 5.0 in (12.8 cm) | 11.25 in (28.8 cm) | 16 in (41.0 cm) |
| Female 2 | Standing | 4.5 in (11.5 cm) | 13.0 in (33.3 cm) | 18.0 in (42.2 cm) |
|  | Sitting | 2.5 in (6.4 cm) | 11.0 in (28.2 cm) | 20.0 in (51.3 cm) |
|  | Lying Down | 5.0 in (12.8 cm) | 12.25 in (31.4 cm) | 17.875 in (45.8 cm) |

Thus, it can be appreciated that while a diaper typically covers the baby from the belly button to the back, the belly button to back distance is significantly shorter than the elongate length of the diaper. As one illustrative example, a medium size diaper is suitable for the baby which was designated Male 2 in Table 1. A medium size diaper, for example a Huggies® Ultratrim Step 3 diaper available from Kimberly-Clark Corporation, has an elongate length of about 17.2 inches (44.1 cm). The belly button to back distance of the Male 2 baby ranged from 10.5 inches (26.9 cm) to 12.0 inches (30.8 cm), depending upon the position of the baby. In order for the liquid control member 44 of diaper 20 of the invention having the same elongate length to remain in contact with the urethral region of the baby throughout this range of movement, the liquid control member desirably reduces the length of the diaper 20 by 6.7 inches (17.2 cm). This amount represents the difference between the elongate length of the diaper, 17.2 inches (44.1 cm), and the smallest measured belly button to back distance for the Male 2 baby, 10.5 inches (26.9 cm).

The required degree of elasticity of the elasticized zone 72 can be expressed in terms of a contracted length of the diaper 20. The contracted length is the unstretched length of the diaper 20 which results from contraction of the elasticized zone 72. One suitable method for determining the contracted length of a diaper is to hang a new diaper 20 vertically adjacent a flat, vertical surface, making sure that handling does not elongate the longitudinally oriented elastic components of the diaper. The diaper is hung with the back waistband region 32 above the front waistband region 30 and with the surface intended to face the wearer during use positioned toward the flat, vertical surface. The top end margin 39 of the diaper 20 is held horizontal with two or more clamps, which are positioned to avoid if possible any absorbent batt of the diaper. Any waist elastic present in the diaper is fully stretched prior to securing the clamps. Thirty minutes after clamping the diaper, the garment shell 42 is transversely cut across its full width in the crotch region 34, as close to the first stationary zone 70 as possible. Care should be used not to cut the liquid control member 44. The contracted length is then determined by measuring the distance between the front and back end edges 28 and 29 along the longitudinal axis 22. No weight is attached to the diaper 20 when measuring the contracted length.

Contraction of the diaper 20, expressed as a percent of the elongate length of the diaper, is determined by subtracting the contracted length from the elongate length 40, and dividing the result by the elongate length. As an example based on the discussion above, a diaper 20 having an elongate length of 17.2 inches (44.1 cm) and a contracted length of 10.5 inches (26.9 cm) is adapted to contract about 39 percent of the elongate length.

In particular embodiments, the elasticity of the elasticized zone 72 can also be understood with reference to the distance between the inward bond points 78 and 79, measured along the liquid control member 44 and along the inner surface 46 of the garment shell 42. The liquid control member 44 is desirably stretched and bonded to the garment shell 42 while in a stretched condition. Alternatively of course, the liquid control member 44 could be bonded to the garment shell 42 while the garment shell is partly or fully folded, pleated, or the like. In either case, the distance between the inward bond points 78 and 79 measured along the surface of the liquid control member 44 while in an unstretched condition can be compared to the distance between the inward bond points 78 and 79 measured along the inner surface 46 of the garment shell 42 also while in an unstretched condition. Desirably, the distance measured along the inner surface 46 of the garment shell 42 exceeds the distance measured along the liquid control member 44 by at least about 10 percent of the elongate length 40, particularly at least about 25 percent of the elongate length, and more particularly at least about 40 percent of the elongate length.

In an alternative embodiment, the liquid control member 44 is stretch bonded to the garment shell 42 so that the first and second stationary zones 70 and 71 contribute to the longitudinal contraction of the diaper 20. More desirably, however, the first and second bond regions 75 and 77 extend only a relatively short distance in the longitudinal direction. For example the first and second bond regions 75 and 77 may comprise less than about 5 percent, and more particularly less than about 2 percent, of the length of the liquid control member 44. In this way, the liquid control member 44 does not tend to bunch the garment shell 42, and more precisely the absorbent assembly 52.

The liquid control member 44 may extend the entire length of the diaper 20 and be attached to the garment shell 42 beginning near the front and back end edges 28 and 29. In the illustrated embodiment, however, the liquid control member 44 extends over only a portion of the elongate length 40 of the diaper 20. The liquid control member 44 desirably extends over less than about 90 percent of the elongate length 40, and particularly from about 70 to about 80 percent of the elongate length for improved performance. In such circumstances, the liquid control member 44 is desirably skewed toward the forward end edge 28 of the diaper 20, and in particular has a front edge coterminously positioned with respect to the front edge of the absorbent assembly 52. For example, the liquid control member 44 may have a length of about 13 inches (33.3 cm) measured in a stretched condition, and the front edge of the liquid control member may be spaced at least about 1 inch (2.6 cm) from the front end edge 30 of the diaper 20.

Figure 4:
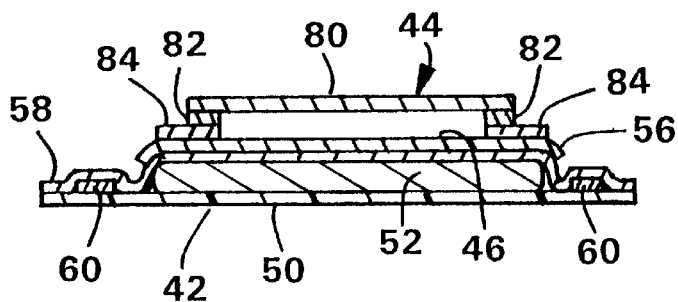
FIG. 4 representatively shows a transverse section view taken generally from the plane of the line 4—4 in FIG. 3.

The illustrated liquid control member 44 includes a liquid handling layer 80, a pair of lateral barriers 82, and a pair of elastic members 84. With reference to FIGS. 3 and 4, the liquid handling layer 80 is directly bonded to the lateral barriers 82. The lateral barriers 82 are spaced from one another and oriented generally along the side edges of the liquid handling layer 80. The elastic members 84 are operatively joined such as by stretch bonding directly to the lateral barriers 82. The first and second bond regions 75 and 77 directly bond the elastic members 84 to the inner surface 46 of the garment shell 42.

The liquid handling layer 80 is formed of a liquid permeable material in order to rapidly accept liquid voids; decelerate the liquid flow; provide transitory capacity; and more slowly discharge liquid to the underlying absorbent. The liquid handling layer 80 and thus the liquid control member 44 is in liquid communication with the absorbent assembly 52 of the garment shell 42. In the illustrated embodiment, the liquid handling layer 80 is in substantially direct liquid contact with the absorbent assembly 52 so that liquid can drain through the liquid handling layer at a controlled rate into the absorbent assembly. As used herein, the term substantially direct liquid contact means that liquid can migrate along the most direct line from any given portion of the liquid handling layer 80 to the absorbent assembly without encountering a substantially liquid impervious material, such as a portion of the backsheet layer 50. Complete direct liquid contact therebetween is not required, because relatively small pieces of liquid impervious material, such as tapes, elastics, or other materials, positioned between the liquid handling layer 80 and the absorbent assembly 52 will not substantially impede liquid movement from the liquid handling layer to the absorbent assembly.

The liquid handling layer 80 may extend the full length of the liquid control member 44 and may include central cutout portions 86 along each side edge. To fit comfortably, the liquid handling layer 80 may have a width dimension between the legs of the wearer, at least in the region of the elasticized zone 72 including the central cutout portions 86, of less than about 4 inches (10.3 cm), particularly less than about 3 inches (7.7 cm), and more particularly from about 1 to about 2 inches (2.6–5.1 cm). Such a narrow width allows the liquid handling layer 80 to slide upward between the legs of the wearer and make good contact with the body. The width of the liquid handling layer 80 is desirably greater at the longitudinal ends, for example at least about 3 inches (7.7 cm), and more particularly at least about 4 inches (10.3 cm) in the first and second stationary zones 70 and 71 for improved performance.

In one aspect of the invention, the liquid handling layer 80 is adapted to rapidly spread liquid throughout the liquid handling layer. Spreading the liquid within the handling layer 80 provides for enhanced utilization of the absorbent assembly 52 when the liquid is subsequently taken up by the garment shell 42. Spreading the liquid in this manner also compensates for the potentially slower uptake rate of the absorbent assembly 52.

Suitable materials for use as the liquid handling layer 80 include a through air bonded carded web. For example, the liquid handling layer 80 may comprise a through air bonded carded web having a basis weight of about 80 to about 360 gsm (grams per square meter) and comprise a blend of 60 percent 6 denier polyester fibers and 40 percent 3 denier polyethylene/polypropylene bicomponent fibers. The liquid handling layer 80 may also comprise a layer of 400 gsm crosslinked cellulose fiber such as sulfonated fibers or naturally crosslinked fibers such as from bleached chemi-thermal-mechanical pulp. This layer could be wrapped in tissue and covered with a polypropylene spunbond layer having a basis weight of about 20 gsm (0.6 osy). The liquid handling layer 80 may also be formed of materials described in relation to the surge management portion 56.

The liquid handling layer 80 works to handle liquid in several ways. First, the fibers slow the velocity of the liquid and diffuse the direction of flow, effectively spreading out the liquid. Secondly, the liquid handling layer 80 takes in liquid until it is saturated in the wetted area. If the liquid handling layer 80 is at an angle to horizontal, the liquid will move by gravity through the material increasing the size of the wetted area. When the wetted area is saturated, any additional liquid delivered to the wetted area will flow rapidly through the liquid handling layer 80 to the absorbent assembly 52 of the garment shell 42.

In one aspect of the invention, the liquid handling layer 80 has a saturated capacity of approximately 10 grams per gram, and particularly about 30 grams per gram. The saturated retention capacity of the liquid handling layer 80 is measured by obtaining and weighing a section of the material. The section of material is then placed on a wire mesh screen and 0.9 percent saline solution is poured over the material until it is saturated. The material is allowed to drain for 30 seconds and is then weighed. The saturated capacity is the difference between the wet weight and the dry weight, divided by the dry weight. In one particular embodiment, the liquid handling layer 80 has a dry weight of approximately 2.8 grams, a saturated capacity of about 30 grams per gram, and thus a theoretical saturated capacity of approximately 85 grams of liquid.

The properties of the liquid handling layer 80 allow the layer to take in liquid quickly, decrease the velocity of the liquid, loosely hold a quantity of liquid, and yet allow the liquid to drain relatively quickly when in contact with an absorbent assembly 52 having a higher capilarity pore structure. Having the above-referenced saturated capacity, however, the liquid handling layer 80 controls the liquid until the absorbent assembly 52 has drawn the liquid away from the liquid handling layer. Further, the ability of the liquid to flow rapidly in the x-y plane of the liquid handling layer 80 under the force of gravity allows for a larger area of the absorbent assembly 52 to be used without relying solely on the rather slow mechanism of wicking.

The lateral barriers 82 are optionally employed to limit leakage past the side edges of the liquid control member 44. The lateral barriers 82 may be formed as strips of material that impede sideways movement of liquid. The lateral barriers 82 may comprise, for example, an absorbent material such as a coform material comprising cellulose fluff and thermoplastic filaments. The lateral barriers 82 desirably have a width dimension measured parallel to the transverse axis 24 of less than about 2 inches (5.1 cm), and particularly about 1 inch (2.6 cm) for improved performance. In the illustrated embodiment, the lateral barriers 82 have cut out outer edges to match the cutout portions 86 of the liquid handling layer 80. The lateral barriers 82 may extend the entire length of the liquid control member 44.

The elastic members 84 of the liquid control member 44 provide the contraction required to keep the liquid control member in contact with the urethral region of the wearer, regardless of whether the wearer is standing, sitting, or lying down. The elasticized zone 72 of the liquid control member 44 in particular can elongate and retract without being encumbered by the components of the garment shell 42, such as the backsheet layer 50, the absorbent assembly 52, the bodyside layer 54, and the leg elastic members 60. The elastic members 84 also function to form seals against the legs of the wearer to also discourage liquid from running down the baby's legs.

The elastic members 84 should possess sufficient elongation potential so that the diaper 20 can be stretched to its elongate length 40. Also, the elastic members 84 should possess sufficient elasticity to contract the diaper 20 to the contracted length referenced above. A suitable material for use as an elastic member 84 should be capable of from about 30 to about 500 percent elongation and upon release of tension will recover at least 80 percent of its elongation. It is generally more desirable for such material to be capable of between about 100 and about 300 percent elongation, particularly at least 200 percent elongation, and recovery upon release of tension of at least 90 percent of its elongation.

One example of a material useful for forming the elastic members 84 is a stretch bonded laminate composed of a prestretched elastic meltblown material such as Kraton G-2755 supplied by Shell Chemical Company of Houston, Tex., sandwiched between spunbond polypropylene webs, each having a basis weight of 13 gsm (0.4 osy).

In the illustrated embodiment, only the side edges of the liquid control member 44 are elasticized by the elastic members 84. Alternatively, a single elastic member (not shown) could be employed. If the width of such single elastic member matched the width of the liquid handling layer 80, the elastic member would desirably be formed of a liquid permeable material to allow liquid to readily transfer to the garment shell 42. The elastic members 84 of the illustrated diaper 20 include straight side edges. At the location of the central cutout portions 86, these straight side edges are transversely spaced outward from the side edges of the liquid handling layer 80 and the lateral barriers 82. Optionally, the side edges of the elastic members 84 may be contoured to match the side edges of the liquid handling layer 80 and the lateral barriers 82, or the latter components may be formed with straight side edges.

The liquid control member 44 desirably has a liquid capacity great enough to accommodate at least about 40 percent of the maximum single void volume projected for the product. Typical urination volumes of babies are presented in Table 2.

TABLE 2

Single Void Volumes

| Baby Age | Average Void | Maximum Void |
|---|---|---|
| 0–4 months | 10–30 ml | 80 ml |
| 3–12 months | 20–50 ml | 150 ml |
| 20–36 months | 40–80 ml | 220 ml |

The liquid control member 44 desirably has a total capacity (described below) of about 15 percent of the total capacity of the garment shell 42. Suitably, the liquid control member 44 has a total capacity of at least about 20 grams and not more than 200 grams. More particularly, the total capacity of the liquid control member 44 should be from about 60 grams to about 200 grams.

The total capacity of the liquid control member 44 and the garment shell 42 are determined as follows. The total capacity of the garment shell 42 is determined using the entire diaper minus the liquid control member 44, which may be severed using a razor blade or scissors. The total capacity of the liquid control member 44 is determined using the liquid control member after having been severed from the garment shell 42. The specimen to be tested is weighed to the nearest 0.1 gram and acclimated at standard relative humidity and temperature for two hours. All elastic components of the specimen are cut so that the specimen lays flat and generally uncontracted. The specimen is then submerged in a container of room temperature (about 23 degrees Celsius) synthetic urine to a minimum depth of 5.1 cm. When testing the garment shell 42, the surface intended to face the wearer during use is positioned downward. The specimen is submerged for a minimum of 20 minutes, but not to exceed 20 minutes and 15 seconds. Next, the specimen is removed from the synthetic urine and placed on a TeflonÔ coated fiberglass screen and allowed to drip for one minute. The surface of the specimen that is intended to face the wearer during use is positioned against the screen. The screen, which has 0.25 inch openings and is commercially available from Taconic Plastics Inc., Petersburg, N.Y., is mounted on a vacuum box. The specimen is then covered with a flexible rubber dam material and a vacuum of 3.5 kilopascals (0.5 pounds per square inch) is drawn in the vacuum box for a period of 5 minutes. The specimen is thereafter removed from the screen and weighed to the nearest 0.1 gram. The capacity of the specimen is determined by subtracting the dry weight of the specimen from the wet weight of the specimen (after application of the vacuum) and is reported in grams of liquid retained.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4$ $7H_2O$), 1.33 grams potassium sulphate ($K_2SO_4$), 1.24 grams tribasic sodium phosphate dodecahydrate ($Na_3PO_4$ $12H_2O$), 4.4 grams sodium chloride (NaCl), 3.16 grams potassium chloride (KCl), 8.56 grams of urea ($CO(NH_2)_2$), 0.1 grams Pluronic 10R8 surfactant (a nonionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the liquid retained by the tea bag material. Suitable tea bag material is a heat sealable tea bag material grade 542, commercially available from Schweitzer-Mauduit International, Inc. The amount of liquid absorbed by the tea bag material is determined by performing the saturated retention capacity test on an empty tea bag. Testing high-absorbency materials or fibers alone can be accomplished using a sealed pouch of tea bag material.

The diaper 20 can be formed in a continuous process by separately forming and then uniting the garment shell 42 and the liquid control member 44. The garment shell 42 can be constructed by supplying continuous backsheet and bodyside materials and sandwiching individual absorbent assemblies 52 between the backsheet and bodyside layers. The peripheries of the backsheet layer 50 and bodyside layer 54 outward of the absorbent assembly 52 can be sealed together, with leg and waist elastic members 60 and 62 operatively connected thereto.

Simultaneously, the components of the liquid control member 44 can be assembled. For instance, the liquid handling layer 80 and the lateral barriers 82 can be bonded together using adhesives, ultrasonic bonds, thermal bonds, mechanical bonds, or the like. The elastic members 84 can then be elongated and bonded in a stretched condition to the liquid handling layer and lateral barriers, using adhesives, ultrasonic bonds, thermal bonds, mechanical bonds, or the like.

With at least the elasticized zone 72 of an individual liquid control member 44 remaining in a stretched condition, the first and second stationary zones can be bonded to the inner surface 46 of the garment shell 42. Individual diapers 20 can then be cut from the continuous supply of backsheet and bodyside materials.

In use, the diaper 20 is positioned on the wearer and secured in place with the tape members 64. The liquid control member 44 remains in contact with the urethral region of the wearer regardless of the position of the wearer. As a result, expelled liquid is not allowed to run freely throughout the diaper but rather immediately contacts the liquid control member 44. The liquid control member 44 is adapted to slow down, channel and/or direct liquid into the absorbent assembly 52 of the garment shell 42. Thus, the diaper 20 need not rely primarily on elasticized leg and waistbands or containment flaps for urine containment.

Figure 7:
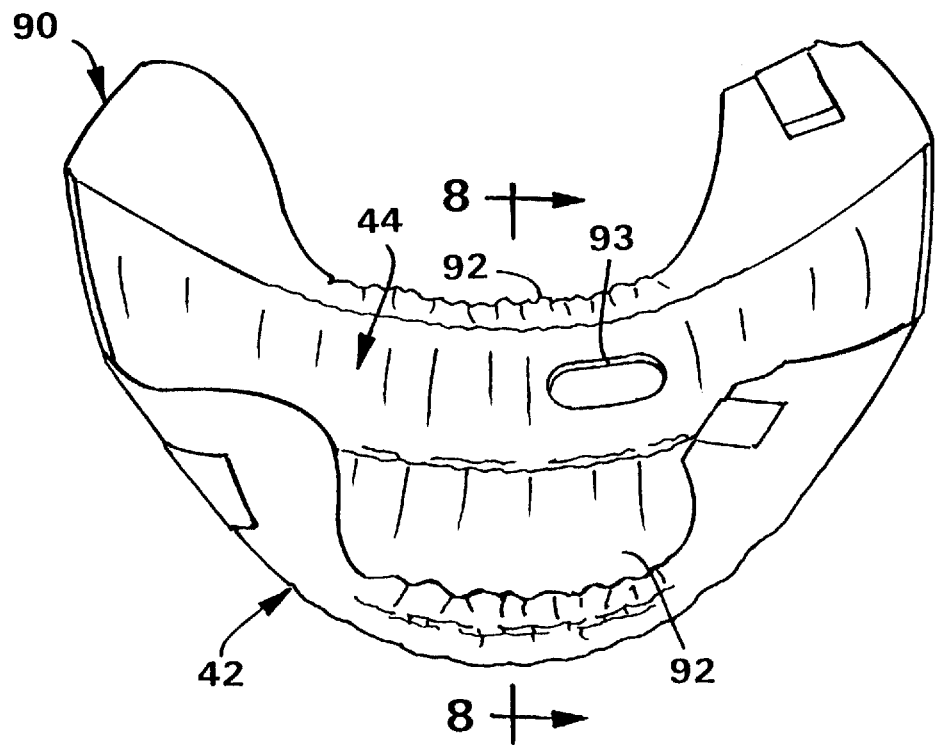
FIG. 7 representatively shows a perspective view of an alternative disposable absorbent article according to the present invention.
Figure 8:
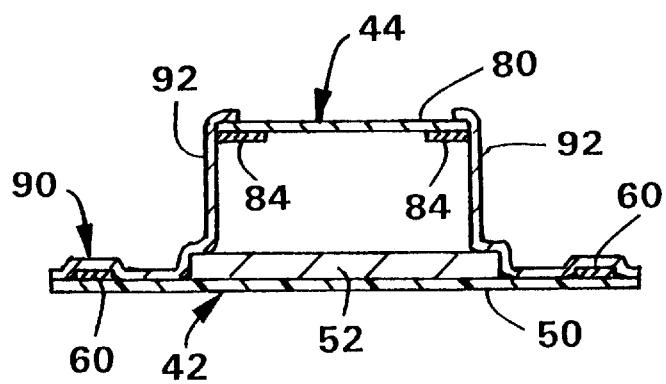
FIG. 8 representatively shows a transverse section view of the absorbent article shown in FIG. 7.

An alternative diaper 90 according to the present invention is illustrated in FIGS. 7 and 8. Components similar to those previously described have been given the same reference numeral. The liquid control member 44 of the diaper 90 is loosely linked to the garment shell 42 by side liner panels 92. The inner edges of the side liner panels 92 are bonded to the liquid control member 44, and the outer edges of the side liner panels are bonded to the garment shell 42. The side liner panels 92 are desirably attached to the garment shell 42 in a folded, pleated or gathered manner so that the panels include surplus material which allows the elasticized zone 72 of the liquid control member 44 to remain in contact with the baby's body.

The side liner panels 92 may be formed of any suitable bodyside liner materials such as 25 gsm (0.75 osy) spunbond polypropylene. No additional bodyside liner material or surge materials may be needed on the bodyside surface of the absorbent assembly 52. Optionally, apertures 93 may be provided in the liquid control member 44 to correspond to the rectal region of the wearer. In this way, some or all of the fecal matter could pass through the liquid control member 44 and be held away from the skin. The side liner panels 92 are desirably hydrophobic in nature to act as partial barriers to expression of liquid from the absorbent assembly 52.

Figure 9:
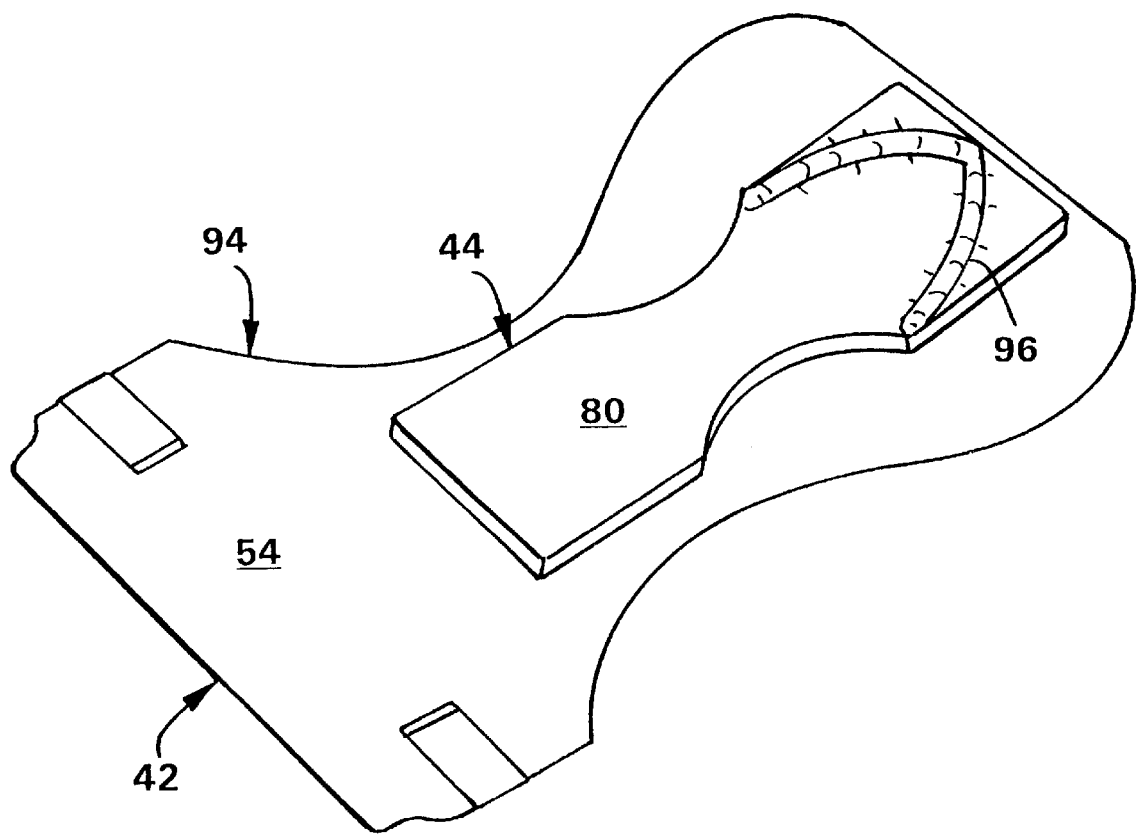
FIG. 9 representatively shows a further alternative disposable absorbent article according to the present invention.

A further alternative embodiment of the invention is illustrated by the diaper 94 in FIG. 9. The diaper 94 includes a thermoformed nonwoven dam 96 that is bonded to the liquid control member 44. The dam 96 assists in preventing liquid from running out the front end of the diaper. The dam 96 may comprise a thermoformable foam, such as a polyethylene foam, and may be bonded to the liquid control member 44 using thermal bonds, adhesive bonds, ultrasonic bonds or other suitable means. In one particular embodiment, the dam 96 is curved and has a height dimension measured perpendicular to the plane of the liquid control member 44 of at least about 1 centimeter.

Figure 10:
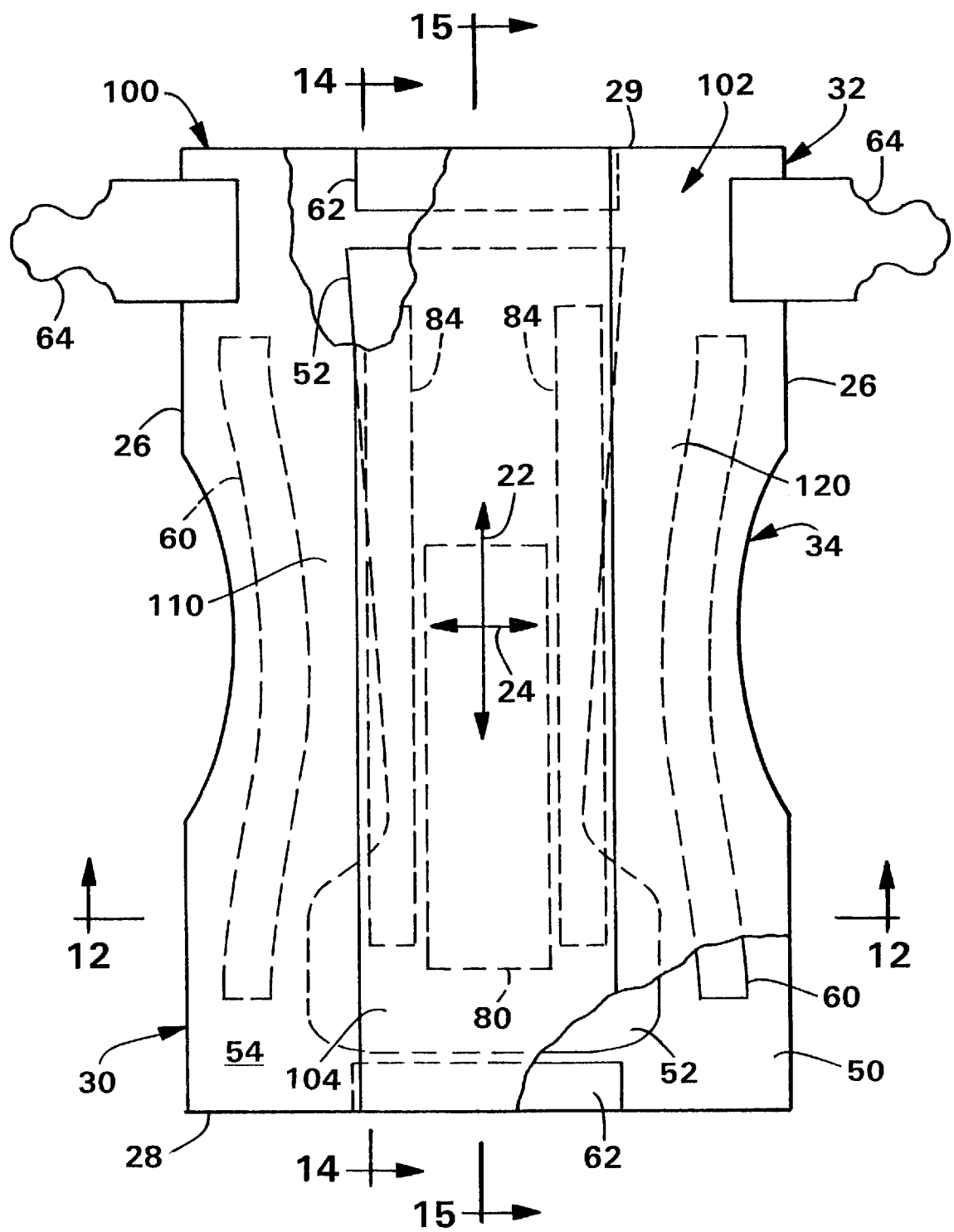
FIG. 10 representatively shows a top plan view of an alternative absorbent article according to the present invention in a stretched flat condition and with portions cut-away for purposes of illustration.
Figure 13:
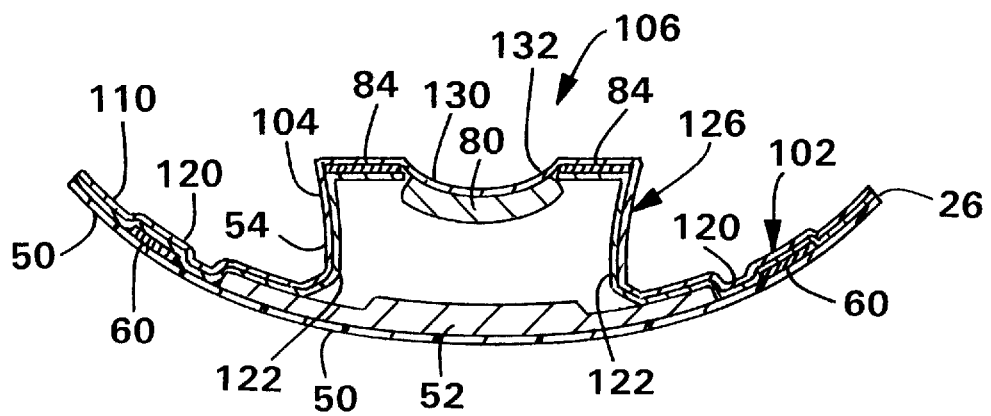
FIG. 13 representatively shows a transverse section similar to FIG. 12, except illustrating the position of the components of the absorbent article when in a relaxed, non-stretched condition.
Figure 15:
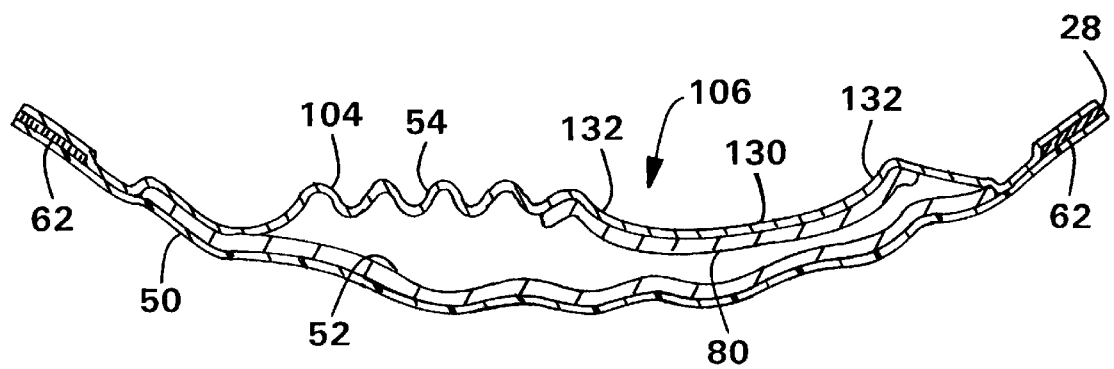
FIG. 15 representatively shows a longitudinal section view taken generally from the plane of the line 15—15 in FIG. 10, but illustrating the position of the components of the absorbent article when in a relaxed, non-stretched condition.

An alternative diaper 100 according to the present invention is illustrated in FIGS. 10–. 15. The diaper 100 desirably comprises a liquid control assembly 102 having a center panel 104 that is adapted to remain in close contact with the urethral region of the wearer. Further, the center panel 104 is adapted to define therein a hammock-shaped portion 106 that conforms with the genitalia of the wearer (FIGS. 13 and 15).

More specifically, the diaper 100 comprises a backsheet layer 50, an absorbent assembly 52 disposed on the backsheet layer, and the liquid control assembly 102 superposed on the backsheet layer. As a result, the absorbent assembly 52 is disposed between the backsheet layer 50 and the liquid control assembly 102. The diaper 100 desirably also includes leg elastic members 60 disposed in the crotch region 34 and extending toward the opposite end edges 28 and 29 and waist elastic members 62 disposed in each of the waistband regions 30 and 32. The diaper 100 is illustrated with refastenable tape members 64 and may also include a tape landing pad 66 (not shown), but may alternatively employ mechanical fastening means as are well known in the art.

Figure 11:
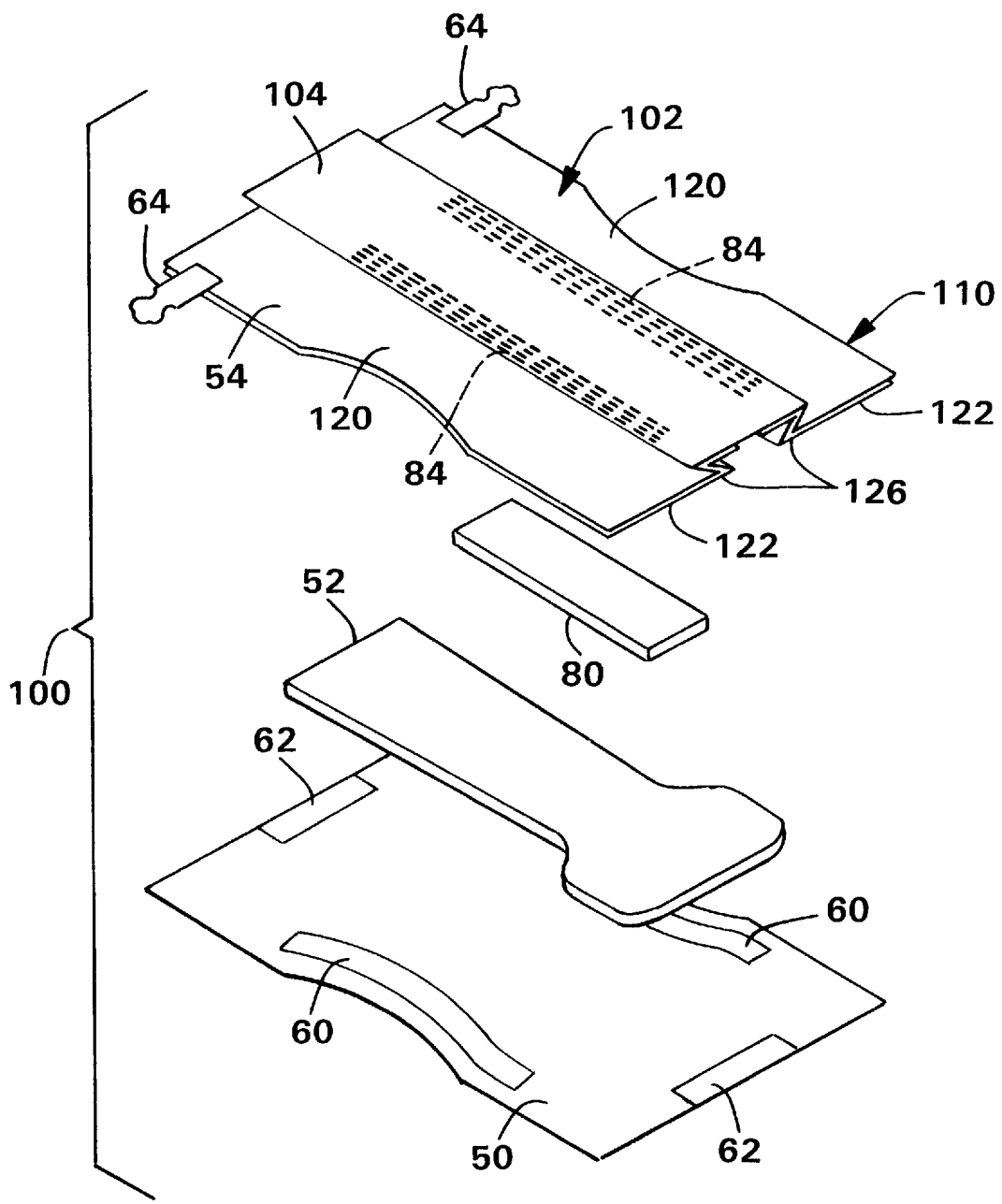
FIG. 11 representatively shows a partially exploded perspective view of the absorbent article of FIG. 10.

The liquid control assembly 102 comprises a liner assembly 110, a pair of liner elastic members 84 and a liquid handling layer 80. The liner assembly 110, which is best viewed in the exploded perspective view of FIG. 11, is divided into the center panel 104 and a pair of lateral panels 120. The center panel 104 is positioned between and interconnects the transversely spaced lateral panels 120.

The liner assembly 110 desirably comprises a bodyside layer 54 and optional barrier layers 122 bonded to the bodyside layer 54. The barrier layers 122 (FIGS. 11–13) are desirably formed of a liquid impermeable material such as polyethylene film or the like. The barrier layers 122 are suitably disposed primarily in the lateral panels 120 and do not extend completely across the center panel 104. It can therefore be seen that the center panel 104 is liquid permeable and allows liquid to enter the diaper 100 for absorption by the absorbent assembly 52, and the lateral panels 120 are liquid impermeable and prevent rewet of the bodyside layer 54. Alternatively, the barrier layers 122 may comprise a material that is liquid permeable but hydrophobic in nature to act as a partial barrier to expression of liquid from the absorbent assembly 52.

The liquid control assembly 102 is bonded to the backsheet layer 50 and optionally to portions of the absorbent assembly 52 as well so that at least a portion of the center panel 104 is capable of movement away from the absorbent assembly 52. In particular, the lateral panels 120 and the longitudinal ends of the center panel 104 are bonded to the backsheet layer 50 and/or the absorbent assembly 52. Between its longitudinal ends, however, the center panel 104 is not bonded to the absorbent assembly 52 so that it is free to move away from the absorbent assembly. The range of movement may also allow limited movement longitudinally and transversely relative to the absorbent assembly 52.

Figure 12:
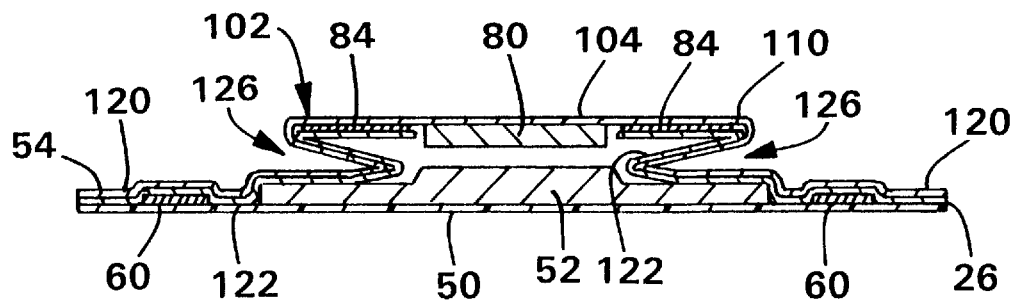
FIG. 12 representatively shows a transverse section view taken generally from the plane of the line 12—12 in FIG. 10.

To facilitate movement of the center panel 104 relative to the absorbent assembly 52, the center panel includes gathered portions 126 or other suitable means for providing spacing between the center panel and the absorbent assembly. With particular reference to FIGS. 11 and 12, the illustrated gathered portions 126 comprise Z-folded portions of the liner assembly 110 that are not bonded to the absorbent assembly 52. The gathered portions 126 enable portions of the center panel 104 and the attached liquid handling layer 80 to move away from the absorbent assembly 52 in response to contraction of the liner elastic members 84. Alternative gathers, pleats, folds, surplus material, elastic materials, or other suitable means may also be used to provide spacing between the center panel 104 and the absorbent assembly 52.

The illustrated liner elastic members 84 are operatively joined to the liner assembly 110 substantially parallel to the longitudinal axis 22 of the diaper 100. The liner elastic members 84 when relaxed are operable to contract the liner assembly 110 to about 40 to about 80 percent, and more particularly to about 50 percent, of its extended length considering only the functionally elastic portions of the elastic material. The liner elastic members 84 are suitably spaced apart by a distance of from about 2.5 to about 10.2 cm., more particularly from about 3.3 to about 9.1 cm., and desirably from about 4.1 to about 8.0 cm., for improved performance. The spacing of the liner elastic members 84 is desirably such that the unadhered center panel 104 can reside against the body of the wearer. The liner elastic members 84 may alternatively be placed in a non-parallel orientation, for instance flared out toward the back waistband region 32 to enhance b.m. containment.

In the longitudinal direction 22, the liner elastic members 84 are desirably located in the target zone of liquid contact. For purposes of the present invention, the "target zone" is considered to comprise an area circumscribed by a circle having a radius of about 6 cm. centered on the point on the diaper liner assembly 110 where urine is expected to strike the diaper 100 when the diaper is placed on a baby as intended. The liner elastic members 84 may extend the full length of the diaper 100 or alternatively less than the full length as illustrated. In particular embodiments, the liner elastic members 84 are sized and positioned to extend from the front waist region 30 to the area of the diaper 100 corresponding to the buttocks of the wearer. Either all or only a portion of the entire length of the liner elastic members 84 may be functionally elastic.

The liquid handling layer 80 is desirably bonded to the bodyside layer 54, for instance on the underside thereof as illustrated, using adhesives, ultrasonic bonds, thermal bonds, or the like. Alternatively, the bodyside layer 54 could define a large aperture or be divided into side panels 92 as illustrated in relation to FIGS. 7 and 8 so that the liquid handling layer 80 is not covered by the bodyside layer 54. Alternatively the liquid handling layer 80 may be bonded to the upperside of the bodyside layer 54. In yet another embodiment the liquid handling layer 80 may be integral to the bodyside layer 54, comprising a region of the bodyside layer 54 with increased basis weight and thickness, rather than a distinct layer.

The liquid handling layer 80 desirably has a width dimension measured parallel to the transverse axis 24 of from about 2.1 to about 9.8 cm, and more particularly from about 2.9 to about 8.7 cm, and desirably from about 3.7 to about 7.6 cm., for improved performance. The liquid handling layer 80 is disposed between the liner elastic members 84, although the sides of the liquid handling layer may extend transversely outward of the liner elastic members (not shown). In the illustrated embodiment the longitudinal sides of the liquid handling layer 80 are disposed transversely inward of the liner elastic members 84 for improved formation of the hammock-shaped portion 106.

The length of the liquid handling layer 80 is desirably selected so that the liquid handling layer does not extend the full length of the center panel 104. For example, the liquid handling layer 80 suitably has a length of from about 10 to about 30 cm., and more particularly from about 13 to about 25 cm., and desirably from about 15 to about 20 cm., for improved performance. The liquid handling layer 80 is desirably positioned in the target zone with the longitudinal ends of the liquid handling layer 80 spaced from the end edges 28 and 29 by at least about 3 cm., and more particularly at least about 5 cm. from the front end edge 28 and at least about 10 cm. from the back end edge 29. The length of the liner elastic members 84 is desirably greater than the length of the liquid handling layer 80.

The liquid handling layer 80 is formed of a liquid permeable material and is in liquid communication, and particularly substantially direct liquid, contact with the absorbent assembly 52. The liquid handling layer 80 comprises a material having an open pore structure to rapidly intake urine, and then rapidly discharge the urine through its thickness dimension into the underlying absorbent assembly 52. The pore size distribution and material composition of the liquid handling layer 80 are selected to provide this functionality. Suitable materials, by way of illustration, may comprise synthetic fiber batts having a density of less than about 0.03 g/cc (grams per cubic centimeter) and a basis weight of at least about 80 gsm (grams per square meter). More particularly, the liquid handling layer 80 may comprise a synthetic fiber batt having a density of from about 0.015 to about 0.025 g/cc and a basis weight of from about 100 to about 300 gsm.

In one aspect of the invention, the diaper 100 allows for the efficient use of the functionally-specific material used to form the liquid handling layer 80. In particular embodiments, for example, the liquid handling layer 80 has a surface area of from about 40 to about 200 $cm^2$ (square centimeters), and more particularly from about 50 to about 150 $cm^2$, and desirably from about 62 to about 100 $cm^2$. In relative terms, the liquid handling layer 80 desirably comprises less than about 25 percent and more particularly less than about 15 percent of the surface area of the extended diaper 100.

In particular embodiments of the invention, the void volume of the liquid handling layer 80 is from about 30 to about 200 $cm^3$, and more particularly from about 40 to about 175 $cm^3$, and desirably from about 50 to about 150 $cm^3$.

The liquid handling layer 80 is bonded to the bodyside layer 54 while the bodyside layer in generally flat and ungathered. In the event the liner elastic members 84 are first bonded to the liner assembly 110, the liner elastic members may be stretched prior to bonding the bodyside layer 54 in place. As the liner elastic members 84 are allowed to relax, the liquid handling layer 80 is deformed from the flat condition illustrated in FIGS. 10 and 12 into the configuration illustrated in FIGS. 13 and 15. Relaxation of the liner elastic members 84 bunches the liquid handling layer 80 to form the hammock-shaped portion 106.

Figure 14:
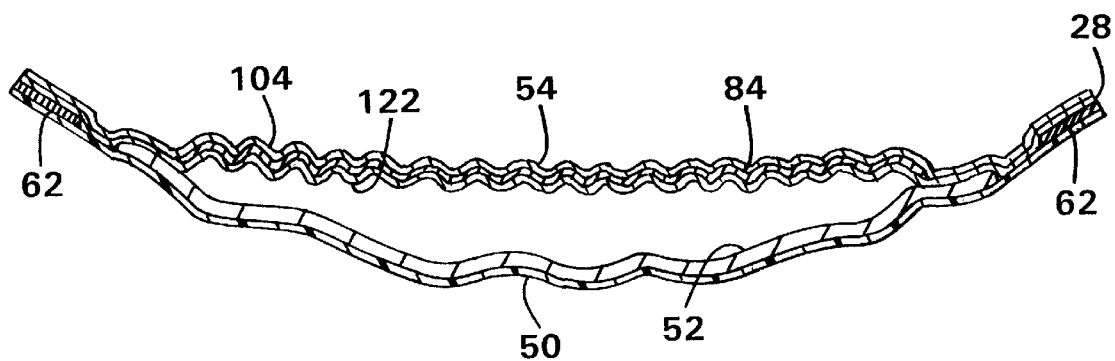
FIG. 14 representatively shows a longitudinal section view taken generally from the plane of the line 14—14 in FIG. 10, but illustrating the position of the components of the absorbent article when in a relaxed, non-stretched condition.

FIGS. 13–15 representatively show several section views of the diaper 100 in a relaxed or unstretched condition. The liner elastic members 84 cause longitudinal gathering of the center panel 104, and in particular of the bodyside layer 54. The liquid handling layer 80 tends to be forced into the void area between the bodyside layer 54 and the absorbent assembly 52. The hammock-shaped portion 106 is consequently concave shaped in both the transverse and longitudinal section views of FIGS. 13 and 15, from the perspective of the bodyside of the diaper 100. The illustrated hammock-shaped portion 106 has a medial region 130 and sidewalls 132 projecting upwardly about the medial region.

The center panel 104 of the liner assembly 110 is adapted to remain in contact with the urethral region of the wearer regardless of the position of the wearer. Expelled liquid is taken in by the liquid handling layer 80, which is adapted to slow down, channel and/or direct liquid into the absorbent assembly 52. The concavity of the hammock-shaped portion 106 functions to cup the genitalia of the wearer, providing intimate contact between the liquid handling layer 80 and the point of urination. The close contact helps ensure that urine rapidly enters the liquid handling layer 80, rather than flowing over the surface of the diaper 100.

The linear velocity (cm/sec) of the urine is at maximum when the urine exits the body. By having the liquid handling layer 80 adjacent the point of urination, this relatively high velocity flow easily penetrates the surface of the bodyside liner. In conventional absorbent article designs, where the surface of the absorbent article may be greater than about 1 to 2 cm. from the point of urination, the urine stream has spread, resulting in a decreased linear velocity when the urine strikes the inner lining of the absorbent article. In such conventional absorbent article designs the lower linear velocity stream of urine has less ability to penetrate the surface of the bodyside liner than in the embodiments of the present invention.

In the event that some of the urine does not immediately enter the liquid handling layer 80, the concave shape ensures that the urine is captured adjacent the body for subsequent penetration into the liquid handling layer. The liner elastic members 84 adjacent the lateral sides of the liquid handling layer 80 may serve as gaskets, restricting the flow of urine to the center panel 104 of the absorbent article 100.

The void volume of the liquid handling layer 80 is typically sufficient to accommodate an individual urination. The importance of this void volume is that even when the absorbency rate of the underlying absorbent assembly 52 is insufficient, such as when the absorbent assembly is already wet with liquid, the liquid handling layer 80 can temporarily accommodate the entire volume of urine from a single urination. That is, it serves as a buffer, taking in the urine as quickly as it is delivered from the wearer, and delivering it more slowly to the absorbent assembly 52.

A wide variety of materials may be used to construct the aforementioned components of the diaper 20. Numerous examples of materials used in constructing absorbent articles are described in the aforementioned U.S. patents incorporated by reference herein. Several components of the disposable absorbent article 20 will now be described in more detail.

The liner 58 presents a body-facing surface which is compliant, soft-feeling, and non-irritating to the wearer's skin. Further, the liner 58 can be less hydrophilic than the absorbent assembly 52, and is sufficiently porous to be liquid permeable, permitting liquid to penetrate through its thickness. The liner 58 has marginal side regions and marginal end regions.

A suitable liner 58 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The liner 58 is typically employed to help isolate the wearer's skin from liquids held in the absorbent assembly 52. Various woven and nonwoven fabrics can be used for the liner 58. For example, the liner may be composed of a meltblown or spunbonded web of polyolefin fibers. The liner may also be a bonded-carded-web composed of natural and/or synthetic fibers.

The liner fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, the liner 58 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% Triton X-102 surfactant. The surfactant can be applied by any conventional means, such as spraying, printing, brush coating or the like.

The surfactant material, such as a conventional wetting agent, can be applied to a medial section of the liner 58 to provide a greater wettability of the medial section, as compared to a remainder of the liner. In particular configurations, the cross-directional width of the medial section can be substantially equal to or less than the cross-directional width of the surge management portion 56. The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The backsheet layer 50 may be composed of a liquid permeable material, but preferably comprises a material which is configured to be substantially impermeable to liquids. For example, a typical backsheet can be manufactured from a thin plastic film, or other flexible liquid-impermeable material. The backsheet 50 prevents the exudates contained in absorbent assembly 52 from wetting articles such as bedsheets and overgarments which contact diaper 20.

In particular embodiments of the invention, the backsheet layer 50 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. The backsheet layer 50 typically provides the outer cover of the article. Optionally, however, the article may comprise a separate outer cover member which is in addition to the backsheet layer.

The backsheet layer 50 may optionally be composed of a micro-porous, "breathable" material which permits vapors to escape from the absorbent assembly 52 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn.

The backsheet layer 50 can also be embossed or otherwise be provided with a matte finish to exhibit a more aesthetically pleasing appearance.

The size of the backsheet layer 50 is typically determined by the size of the absorbent assembly 52 and the exact diaper design selected. The backsheet layer 50, for example, may have a generally T-shape, a generally I-shape or a modified hourglass shape, and may extend beyond the terminal edges of the absorbent assembly 52 by a selected distance, such as a distance within the range of about 1.3 centimeters to 2.5 centimeters (about 0.5 to 1.0 inch), to provide side margins.

The liner 58 and backsheet layer 50 are connected or otherwise associated together in an operable manner. As used therein, the term "associated" encompasses configurations in which the liner 58 is directly joined to the backsheet layer 50 by affixing liner 58 directly to the backsheet, and configurations wherein the liner is joined to the backsheet by affixing the liner to intermediate members which in turn are affixed to the backsheet. The liner 58 and backsheet layer 50 can be affixed directly to each other in the diaper periphery 36 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix liner 58 to backsheet layer 50.

It should be readily appreciated that the above-described attachment means may also be employed to interconnect and assemble together the various other component parts of the article described herein.

An absorbent body, such as absorbent assembly 52, is positioned between the liner 58 and backsheet layer 50 to form the diaper 20. The absorbent assembly 52 has a construction which is generally compressible, conformable, non-irritating to the wearer's skin, and capable of absorbing and retaining liquid body exudates. It should be understood that, for purposes of this invention, the absorbent assembly 52 may comprise a single, integral piece of material, or alternatively, may comprise a plurality of individual separate pieces of material which are operably assembled together.

Various types of wettable, hydrophilic fibrous material can be used to form the component parts of absorbent assembly 52. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The absorbent assembly 52 can, for example, comprise a matrix of hydrophilic fibers, such as a web of cellulosic fluff, mixed with particles of high-absorbency material. In particular arrangements, the absorbent assembly 52 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent assembly include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent assembly 52 is generally in the form of discrete particles. The particles can be of any desired shape, for example, spiral or semi-spiral, cubic, rod-like, polyhedral, and so forth. Shapes having a large greatest dimension/smallest dimension ratio, like needles, flakes, and fibers, are also contemplated for use herein. Conglomerates of particles of absorbent gelling material may also be used in the absorbent assembly 52.

Preferred for use are particles having an average size of from about 20 microns to about 1 millimeter. "Particle size" as used herein means the weighted average of the smallest dimension of the individual particles.

Suitable high-absorbency materials and absorbent structures incorporating such materials are described in detail in U.S. patent application Ser. No. 757,787 of S. Byerly et al., entitled "ABSORBENT COMPOSITES AND ABSORBENT ARTICLES CONTAINING SAME" and filed on Sep. 11, 1991 (Attorney Docket No. 10174); U.S. Pat. No. 5,147,343 issued Sep. 15, 1992, to Kellenberger; and European Patent Application EP 0 339 461 A1, published Nov. 2, 1989; the disclosures of which are hereby incorporated by reference in a manner that is consistent with the present specification.

An example of a superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

In a particular embodiment of the invention, absorbent assembly 52 can be generally T-shaped with the laterally extending cross-bar of the "T" generally corresponding to the front waistband region 30 of the absorbent article for improved performance, especially for male infants. In the illustrated embodiments, for example, the assembly 52 across the ear section of the front waistband region 30 of the article has a cross-directional width of about 23 cm (9 in), the narrowest portion of the crotch section has a width of about 9 cm (3.5 in) and the back waistband region 32 has a width of about 11.4 cm (4.5 in).

The entire absorbent assembly 52, or any individual portion thereof, can be overwrapped in a hydrophilic high wet-strength envelope web, such as a high wetstrength tissue or a synthetic fibrous web (not shown). Such overwrapping web can also increase the in-use integrity of the absorbent assembly 52. The web can be suitably bonded, such as with adhesive, to other portions of the assembly and to other components of the product construction. The overwrapping web may comprise a multi-element wrapsheet which includes a separate bodyside wrap layer and a separate outside wrap layer, each of which extends past all or some of the peripheral edges of absorbent portion. Such a configuration of the wrap sheet can, for example, facilitate the formation of a substantially complete sealing and closure around the peripheral edges of absorbent portion. The bodyside and outside layers of wrap sheet may be composed of substantially the same material, or may be composed of different materials. Suitable materials for constructing such an overwrapping web are disclosed in previously incorporated U.S. patent application Ser. No. 08/168,615 by T. Roessler et al., filed Dec. 16,1993, and titled "Dynamic Fitting Diaper" (Attorney Docket No. 10,961).

Optionally, the garment shell 42 may include a porous, liquid-permeable layer of surge management material 56 to advantageously improve the overall uptake rate of the composite absorbent assembly 52. Surge management portion 56 is typically less hydrophilic than absorbent assembly 52, and has an operable level of density and basis weight to quickly collect and temporarily hold liquid surges, and to transport the liquid from its initial entrance point and release the liquid to other parts of the absorbent assembly 52.

Various woven and nonwoven fabrics can be used to construct surge management portion 56. For example, the surge management portion may be a layer composed of a meltblown or spunbonded web of polyolefin fibers. The surge management layer may also be a bonded-carded-web or an airlaid web composed of natural and synthetic fibers.

The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inches. The surge management portion 56 may be composed of a substantially hydrophobic material, and the hydrophobic material may optionally be treated with a surfactant or otherwise processed to impart a desired level of wettability and hydrophilicity. Suitable materials for use as a surge management portion 56 are disclosed in previously incorporated U.S. patent application Ser. No. 08/168,615 by T. Roessler et al., filed Dec. 16, 1993, and titled "Dynamic Fitting Diaper" (Attorney Docket No. 10,961).

As representatively shown, surge management portion 56 may be configured for placement adjacent an outwardly facing, outerside of liner 58. Optionally, the surge management portion 56 can be placed adjacent an inwardly facing, bodyside surface of liner 58. The absorbent assembly 52 is positioned in liquid communication with surge management portion 56 to receive liquids released from the surge management portion, and to hold and store the liquid. The optional surge management portion 56 serves to quickly collect and temporarily hold discharged liquids, to transport such liquids from the point of initial contact and spread the liquid to other parts of the surge management portion, and then to substantially completely release such liquids into the layer or layers comprising absorbent assembly 52.

A capillary force differential created at the interface between the absorbent assembly 52 and the material immediately adjacent the bodyside of the absorbent assembly can improve the containment characteristics of garment shell 42. For example, if the surge management portion 56 is composed of a layer positioned immediately adjacent to the absorbent assembly 52, and if the surge layer is appropriately configured to provide and maintain a relatively lower capillary attraction, as compared to the capillary attraction exhibited by absorbent assembly 52, then liquid surges tend to be desorbed more readily from the surge management portion and into the absorbent assembly. Because absorbent assembly 52 can thereby have a relatively higher capillarity than surge management portion 56, the liquid surges tend to be drawn into absorbent assembly 52 and distributed to the more remote regions thereof by wicking along the plane generally defined by the absorbent assembly.

Additional details regarding the surge materials are set forth in U.S. Pat. No. 5,486,166 issued Jan. 23, 1996, to C. Ellis and D. Bishop; and U.S. Pat. No. 5,490,846 issued Feb. 13, 1996, to C. Ellis and R. Everett; the disclosures of which are hereby incorporated by reference in a manner that is consistent herewith. In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

The leg and waist elastic members 60 and 62 are typically secured to the diaper 20 in an elastically contractible condition so that in a normal, under-strain configuration, the elastic members effectively contract against the diaper. These elastic members 60 and 62 can be secured in an elastically contractible condition in at least two ways, for example, the elastic members may be stretched and secured while the diaper 20 is in an uncontracted condition. Alternatively, the diaper 20 may be contracted, for example, by pleating, and the elastic members secured and connected to the diaper while the elastic members are in their relaxed or unstretched condition. Still other means, such as heat-shrink elastic material, may be used to gather the garment.

In the embodiment illustrated in FIGS. 1–3, the leg elastic members 60, in combination, extend essentially along the complete length of the crotch region 34 of the diaper 20. Alternatively, the elastic members 60 may extend the entire length of the diaper 20, or any other length suitable for providing the arrangement of elastically contractible lines desired for the particular diaper design.

The elastic members 60 and 62 may have any of a multitude of configurations. For example, the width of the individual elastic members may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to the garment shell 42 with sprayed or swirled patterns of hotmelt or other type of adhesive.

In particular configurations, for example, the leg elastic members 60 may comprise a carrier sheet to which are attached a grouped set of elastics composed of a plurality of individual elastic strands (not shown). The elastic strands may intersect or be interconnected, or be entirely separated from one another. The carrier sheet may, for example, comprise a 0.002 cm thick film of unembossed polypropylene material. The elastic strands can, for example, be composed of LYCRA® elastomer available from DuPont, a business having offices in Wilmington, Del. Each elastic strand is typically within the range of about 420-1050 decitex (dtx), and preferably, is about 940 dtx in an embodiment of the invention wherein three strands are employed for each elasticized legband. In addition, leg elastics 34 may be generally straight or optionally curved.

The various configurations of the invention can optionally include elasticized containment flaps (not shown). The garment shell 42 may, for instance, include two containment flaps which are connected to the bodyside layer 54. Suitable constructions and arrangements for containment flaps are described, for example, in U.S. Pat. No. 4,704,116 issued Nov. 3, 1987, to K. Enloe, the disclosure of which is hereby incorporated by reference in a manner that is consistent herewith. Other configurations of the containment flaps are described in U.S. patent application Ser. No. 208,816 of R. Everett et al., filed Mar. 4, 1994 and entitled "ABSORBENT ARTICLE HAVING AN IMPROVED SURGE MANAGEMENT" (Attorney docket No. 11,375), the disclosure of which is hereby incorporated by reference in a manner that is consistent herewith.

The following EXAMPLES are provided to give a more detailed understanding of the invention. The particular amounts, proportions, compositions and parameters are meant to be exemplary, and are not intended to specifically limit the scope of the invention.

EXAMPLE 1

A diaper 20 as shown in FIG. 1 was constructed to illustrate particular features and advantages of the present invention. The diaper 20 included a garment shell 42 including a backsheet layer 50, a bodyside layer 54, and an absorbent assembly 52 disposed between the backsheet and bodyside layers. The backsheet and bodyside layers 50 and 54 covered the major surfaces of the absorbent assembly 52 and were sealed together along their lateral side edges and end edges. The bodyside layer 54 included a full-width liner 58 and a narrower surge management portion 56 bonded to the liner on the surface opposite the absorbent assembly 52. The garment shell 42 also included leg elastic members 60, waist elastic members 62, and a tape fastening system 64 and 66.

The diaper 20 also included a liquid control member 44 bonded to the inner surface 46 of the garment shell 42. The liquid control member 44 included a liquid handling layer 80, a pair of lateral barriers 82, and a pair of elastic members 84. The liquid handling layer 80 comprised a mat of a 3-¼ inch (8.3 cm) by 12 inch (30.5 cm) layer and two 8 inch (20.3 cm) by 2 inch (5.1 cm) layers of 120 gsm through air bonded carded web composite fabric. The web was composed of a blend containing 40 percent 6 denier polyester fibers and 60 percent 3 denier polypropylene/polyethylene bicomponent fibers. The lateral barriers 82 were in the form of 1 inch (2.5 cm) by 12 inch (30.5 cm) strips of 126 gsm spunbond coform material comprising cellulose and meltblown fibers. The elastomeric members 84 were 1 inch (2.5 cm) by 6 inch (15.2 cm) strips of stretch bonded laminate material elongated to 12 inches (30.5 cm) and attached to the other components of the liquid control member 44. The stretch bonded laminate comprises a layer of elastic material sandwiched between spunbond webs.

The backsheet layer 50 was composed of a 0.03 mm (1.25 mil) thick polyethylene film containing $TiO_2$ for increased opacity. The liner 58 was a nonwoven, spunbond polypropylene fabric composed of about 2.8–3.2 denier fibers formed into a web having a basis weight of about 20 g/m². The fabric was surface treated with about 0.27% Triton X-102 surfactant. The absorbent assembly 52 had a matrix of cellulose fibers mixed with superabsorbent particles. Bodyside and outerside wrap layers formed of cellulose tissue webs covered the absorbent matrix. The leg elastic members 60 were composed of a carrier sheet to which 4 strands of 740 decitex LYCRA elastomer were attached. The leg elastics members 60 were curved such that the elastic members bowed inwardly at the crotch portion of the diaper 20. The surge management portion 56 was a through-air-bonded-carded web, composite fabric. The web was composed of a blend containing 40% of 6 denier polyester fibers and 60% of 3 denier polypropylene/polyethylene bicomponent fibers, and had an overall basis weight of about 51 gsm. The waist elastic members 62 had a longitudinal dimension of approximately 25 mm and a lateral dimension of approximately 102 mm, as measured with the diaper in its flat-out condition. The waist elastic members 62 were located at each longitudinal ends of the diaper, and were composed of an elastomeric stretch-bonded-laminate fabric of approximately 72 gsm total basis weight. The fabric contained a meltblown fiber core of approximately 45 gsm basis weight sandwiched between two polypropylene spunbond facing layers, with each facing layer having a basis weight of approximately 13 gsm.

EXAMPLE 2

A diaper designated a control diaper was also tested. The control diaper was identical to diaper 20 of the Example 1 except that: no liquid control member 44 was used; the control diaper included elasticized containment flaps; and the surge material in the control diaper was 4 inches (10.2 cm) wide and 9 inches (22.9 cm) long and placed under the liner 2 inches (5.1 cm) from the front end of the absorbent assembly. The control diaper corresponded to a HUGGIES® Ultratrim Step 3 diaper as available from Kimberly-Clark Corporation on about Aug. 1, 1994.

For purposes of analyzing the performance of the diapers 20, a forced failure test was conducted. The test used twenty babies who were each fitted with a fabric belt which contains a flexible latex tube extending from the back waist of the belt to the urethral region of the baby. The babies were then fitted with one of the diapers and also a cover pant. The cover pant comprised a dark colored, cotton, washable pant with leg cuffs and waist elastics, such as can be purchased from the J. C. Penney Company. Subsequently, each diaper was loaded through the tube with an initial load of 60 cc of saline having a temperature of 92 to 96 degrees Fahrenheit (33°–36° C.). After a minimum of 10 minutes, a subsequent load of 60 cc of saline is input through the tube. The step of waiting 10 minutes and adding an additional load of 60 cc of saline is repeated until leakage occurs. Leakage constituted the identification of wet areas on the cover pant. This procedure was repeated on subsequent days using a different example diaper.

The results of the forced failure test are presented in Table 3. Dashed lines indicate that no data was available, because the diaper contained fecal material, the baby was unavailable on the designated test day, or the like.

TABLE 3

| | Liquid Content at Failure | | | | | | | |
|---|---|---|---|---|---|---|---|---|
| | Control | | | | Diaper 20 | | | |
| Baby | Stand | Sit | Prone | Supine | Stand | Sit | Prone | Supine |
| | | | | MALE | | | | |
| B1 | 332.8 | 171.9 | 336.1 | 221.6 | 371.5 | 381.8 | — | — |
| B2 | 231.9 | 235.7 | 171.3 | 89.8 | 364.1 | 369.7 | 262.6 | 303.3 |
| B3 | 239.3 | 234.3 | 216.8 | 174.6 | 362.7 | 358.3 | 278.7 | 263.6 |
| B4 | 336.8 | 345.2 | 181.5 | 343.7 | 366.3 | 266.2 | 430.8 | 376.9 |
| B5 | 119.7 | 199.0 | 178.0 | 114.7 | 308.4 | 305.4 | 181.7 | 309.1 |
| B6 | 307.2 | — | 119.3 | 119.9 | 425.7 | 362.7 | 369.8 | — |
| B7 | 278.8 | 180.1 | 302.5 | 226.8 | 359.7 | 432.0 | 304.5 | 340.2 |
| B8 | 59.9 | 231.1 | 362.4 | 303 | 313.0 | 304.9 | 364.9 | 234.0 |
| B9 | 286.4 | 148.4 | 148.7 | 271.9 | 369.2 | 229.1 | 326.4 | 204.3 |
| B10 | 179.8 | 182 | 137.4 | 317.1 | 365.2 | 371.1 | 420.7 | 290.4 |
| Avg. | 237.3 | 214.2 | 215.4 | 218.3 | 360.6 | 338.1 | 326.7 | 290.3 |
| | | | | FEMALE | | | | |
| F1 | 180.1 | 185.5 | 279.9 | 186.6 | — | 218.5 | 184.9 | 348.6 |
| F2 | 181.5 | 149.2 | 239.8 | 173.8 | 304.3 | 222 | 344.0 | 266.8 |
| F3 | 117.4 | 115.2 | 182 | 177.0 | 246 | 243.4 | 303.7 | 299.4 |
| F4 | 195.8 | 141.7 | 205.8 | 123.1 | 306.1 | 296.8 | 347.3 | 245.4 |
| F5 | 292.3 | 119.3 | 233.1 | 236 | 423.9 | — | 182.1 | 258.6 |
| F6 | 163.0 | 323.2 | 239.2 | 322 | 368 | 420.9 | 360.5 | 364.2 |
| F7 | 295.6 | 115.9 | 191.1 | 183.7 | 436.4 | 319 | 415 | 304.4 |
| F8 | — | 180.9 | 234.0 | 268.8 | 404.5 | 405.3 | 368.5 | 301.7 |
| F9 | 276.0 | 268.4 | 264.1 | 182.4 | 292.9 | 313.9 | 334.9 | 274.0 |
| F10 | 265.1 | 189.2 | 257.1 | 212.7 | 315.7 | 161.3 | 440.1 | 382.5 |
| Avg. | 218.5 | 178.9 | 232.4 | 206.6 | 344.2 | 289 | 328.1 | 304.6 |

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article having a longitudinal axis, an elongate length, a first waistband region, a second waistband region, and an intermediate region interconnecting the first and second waistband regions, the absorbent article comprising:

a garment shell comprising a backsheet layer, an absorbent assembly disposed on the backsheet layer, and a bodyside layer bonded to the backsheet layer and sandwiching the absorbent assembly therebetween; and a liquid control member having a first stationary zone bonded to the bodyside layer in the first waistband region, an opposite second stationary zone bonded to the bodyside layer in the second waistband region, and an elasticized zone between the first and second stationary zones, the elasticized zone adapted to contract at least about 10 percent of the elongate length, the liquid control member comprising:

a liquid permeable liquid handling layer in substantially direct liquid contact with the absorbent assembly and configured to have a saturated retention capacity of at least about 10 grams per gram and to permit liquid to drain through the liquid handling layer into the absorbent assembly, the absorbent assembly having a smaller pore size than the liquid handling layer, the liquid handling layer having a width dimension in the elasticized zone of less than about 3 inches; and a pair of elastic members disposed along opposite sides of the liquid handling layer.

2. The absorbent article of claim 1, wherein the elasticized zone is adapted to contract the absorbent article at least about 25 percent of the elongate length.

3. The absorbent article of claim 1, wherein the liquid control member further comprises a pair of lateral barriers formed of an absorbent material and bonded to the liquid handling layer.

4. The absorbent article of claim 1, wherein the liquid control member is longitudinally skewed toward a first end edge of the absorbent article.

5. The absorbent article of claim 1, wherein the liquid control member has a total capacity of about 15 percent of a total capacity of the garment shell.

6. The absorbent article of claim 1, wherein the liquid control member has a total capacity of at least about 20 grams and not more than about 200 grams.

7. The absorbent article of claim 1, wherein the liquid control member defines an aperture adapted to receive fecal matter.

8. The absorbent article of claim 1, further comprising side liner panels having opposite inner and outer edges, the inner edges bonded to the liquid control member and the outer edges bonded to the garment shell.

9. The absorbent article of claim 8, wherein the side liner panels are hydrophobic in nature.

10. The absorbent article of claim 1, further comprising a dam of formable material bonded to the liquid control member.

11. The absorbent article of claim 1, wherein the liquid handling layer has a width dimension in the elasticized zone of from about 1 to about 2 inches.

* * * * *